United States Patent
van Dijk et al.

(10) Patent No.: US 6,558,905 B1
(45) Date of Patent: *May 6, 2003

(54) DIAGNOSTICS AND THERAPEUTICS FOR OSTEOPOROSIS

(75) Inventors: Simon van Dijk, San Antonio, TX (US); Gordon W. Duff, Sheffield (GB)

(73) Assignee: Interleukin Genetics, Inc., Waltham, MA (US)

( * ) Notice: Subject to any disclaimer, the term of this patent is extended or adjusted under 35 U.S.C. 154(b) by 167 days.

This patent is subject to a terminal disclaimer.

(21) Appl. No.: 09/650,785

(22) Filed: Aug. 30, 2000

Related U.S. Application Data

(60) Provisional application No. 60/151,460, filed on Aug. 30, 1999.

(51) Int. Cl.⁷ .......................... C12Q 1/68; C12P 19/34; C07H 21/02; C07H 21/04
(52) U.S. Cl. ................. 435/6; 435/91.2; 536/22.1; 536/23.1; 536/25.3; 514/12
(58) Field of Search ................ 435/6, 91.1, 91.2; 536/22.1, 24.3, 24.31, 24.33; 514/1.2

(56) References Cited

U.S. PATENT DOCUMENTS

| | | | | |
|---|---|---|---|---|
| 4,656,127 A | | 4/1987 | Mundy | ..................... 435/6 |
| 5,698,399 A | * | 12/1997 | Duff et al. | |
| 6,268,142 B1 | * | 7/2001 | Duff et al. | |

FOREIGN PATENT DOCUMENTS

| | | |
|---|---|---|
| WO | WO 88/09457 | 12/1988 |
| WO | WO 91/02087 | 2/1991 |
| WO | WO 93/11149 | 6/1993 |
| WO | Wo 94/03633 | 2/1994 |
| WO | WO 94/14844 | 7/1994 |
| WO | WO 94/20615 | 9/1994 |
| WO | WO 95/01995 | 1/1995 |
| WO | WO 98/44150 | 10/1998 |
| WO | WO 98/54359 | 12/1998 |

OTHER PUBLICATIONS

Abremski, Ken et al., "Bacteriophage P1 Site–specific Recombination", The Journal of Biological Chemistry 259 (3): 1509–1514 (Feb. 10, 1984).

Barany, Francis, "Genetic Disease Detection and DNA Amplification Using Cloned Thermostable Ligase", Proc. Natl. Acad. Sci. USA 88: 189–193 (Jan. 1991).

Blakemore, Alexandra I. F. et al., "Association of Graves' Disease with an Allele of the Interleukin–1 Receptor Antagonist Gene", Journal of Clinical Endocrinology and Metabolism 80 (1): 111–115 (199%).

Blakemore, Alexandra I. F. et al., "Interleukin–1 Receptor Antagonist Allele (IL1RN*2) Aociated with Nephropathy in Diabetes Mellitus", Hum Genet 97:369–374 (1996).

Blakemore, Alexandra I. F. et al., "Interleukin–1 Receptor Antagonist Gene Polymorphism as a Disease Severity Factor in Systemic Lupus Erythematosus", Arthritis & Rheumatism 37 (9): 1380–1385 (Sep. 1994).

Bradley, Allan et al., "Formation of Germ–line Chimaeras from Embryo–derived Teratocarcinoma Cell Lines", Nature 309:255–256 (May 17, 1984).

Brinster, Ralph et al., "Factors Affecting the Efficieny of Introducing Foreign DNA into Mice by Microinjecting Eggs", Proc. Natl. Acad. Sci. USA 82:4438–4442 (Jul. 1985).

Clark, Burton D. et al., "Genomic Sequence for Human Prointerleukin 1 Beta: Possible Evolution from a Reverse Transcribed Prointerleukin 1 Alpah Gene", Nucleic Acids Research 14(20):7897–7914 (1986).

Clay, Frances E. et al., "Interleukin 1 Receptor Antagonist Gene Polymorphism Association with Lichen Sclerosus", Hum Genet 94: 407–410 (1994).

Clay, Frances E. et al., "Novel Interleukin–1 Receptor Antagonist Exon Polymorphisms and their Use in Allele–specific MRNA Assessment", Hum Genet 97:723–726 (1996).

Cork, Michael J. et al., "An Allele of the Interleukin–1 Receptor Antagonist as a Genetic Severity Factor in Alopecia Areata", Journal of Investigative Dermatology 104 (5) Supp.: 158–159 (May 1995).

Cotton, R. G. H., "Current Methods of Mutation Detection", Mutation Research 285: 125–144 (1993).

Cotton, Richard G. H., "Reactivity of Cytosine and Thymine in Single–base–pair Mismatches with Hydroxylamine and Osmium Tetroxide and its Application to the Study of Mutations", Proc. Natl. Acad. Sci. USA 85: 4397–4410 (Jun. 1988).

Eastell, R. et al., "IL–1 Receptor Antagonist Genotype is Associated with Low Bone Mineral Density in Postmenopausal Osteoporosis", (1998) Bone 23 (5s):S375.

Evans, M. J. et al., "Establishment in Culture of Pluripotential Cells from Mouse Embryos", Nature 292: 154–156 (Jul. 9, 1981).

Gibbs, Richard A. et al., "Detection of Single DNA Base Differences by Competitive Oligonucleotide Printing", Nucleic Acids Research 17 (7): 2437–2448 (1989).

Gossler, Achim et al., "Transgenesis by Means of Blastocyst–derived Embryonic Stem Cell Lines", Proc. Natl. Acad. Sci. USA 83: 9065–9069 (Dec. 1986).

(List continued on next page.)

Primary Examiner—W. Gary Jones
Assistant Examiner—Arun Kr. Chakrabarti
(74) Attorney, Agent, or Firm—Foley Hoag, LLP; Beth E. Arnold; James T. Olesen

(57) ABSTRACT

Diagnostics and therapeutics for osteoporosis, which are based on the identification of the subject's IL-1 haplotype pattern are described.

4 Claims, 5 Drawing Sheets

OTHER PUBLICATIONS

Guatelli, John C. et al., "Isothermal, In Vitro Amplification of Nucleic Acids by a Multienzyme Reaction Modeled after Retroviral Replication", Proc. Natl. Acad. Sci. USA 87:1874–1878 (Mar. 1990).

Hart, Thomas C. et al., "Genetic Factors in the Pathogensis of Periodontitis", Periodontology 2000 14: 202–215 (1997).

Hsu, Ih–Chang et al., "Detection of DNA Point Mutations with DNA Mismatch Repair Enzymes", Carcinogenesis 15(8): 1657–1662 (1994).

Jaenisch, Rudolf, "Germ Line Integration and Mendelian Transmission of the Exogenous Moloney Leukemia Virus", Proc. Natl. Acad. Sci. USA 73 (4): 1260–1264 (Apr. 1976).

Jaenisch, Rudolf, "Transgenic Animals" Science 240: 1468–1474 (Jun. 10, 1988).

Jahner, Detlev et al., "De novo Methylation and Expression of Retroviral Genomes During Mouse Embryogenesis", Nature 298: 623–628 (Aug. 12, 1982).

Keen, R. W. et a., "Allelic Variation at the Interleukin–1 Receptor Antagonist Genet Associated with Early Postmenopausal Bone Loss at the Spine", Bone 23 (4): 367–371 (Oct. 1998).

Kornher, J. Stephen et al., "Mutation Detection using Nucleotide Analogs that Alter Electrophoretic Mobility", Nucleic Acids Research 17(19): 7779–7784 (1989).

Kornman, Kenneth S. et al., "Genetic Variations in Cytokine Expression: A Risk Factor for Severity of Adult Periodontitis", Ann Periodont 3(1) 327–338 (Jul. 1998).

Kornman, Kenneth S. et al., "The Interleukin–1 Genotype as a Severity Factor in Adult Periodontal Disease", J Clin Periodontol 24: 72–77 (1997).

Kuppuswamy, Mohan N. et al., "Single Nucleotide Primer Extention to Detect Genetic Disease: Experimental Application to Hemophilia B (Factor IX) and Systic Fibrosis Genes", Proc. Natl. Acad. Sci. USA 88: 1143–1147 (Feb. 1991).

Kwoh, D. Y. et al., "Transcription–based Amplification System and Detection of Amplified Human Immunodeficiency Virus Type 1 with a Bead–based Sandwich Hybridization Format", Proc. Natl. Acad. Sci. USA 86: 1173–1177 (Feb. 1989).

Lasko, M. et al., "Targeted Oncogene Activation by Site–specific Recombination in Transgenic Mice", Proc. Natl. Acad. Sci. USA 89: 6232–6236 (Jul. 1992).

Landegren, Ulf et al., "A Ligase–Mediated Gene Detection Technique", Science 241: 1077–1080 (Aug. 26, 1988).

Mansfield, John C. et al., "Novel Genetic Association Between Ulcerative Colitis and the Anti–inflammatory Cytokine Interleukin–1 Receptor Antagonist", Gastroenterology 106: 637–642 (1994).

Maxam, Allan M. et al., "A New Method for Sequencing DNA", Proc. Natl. Acad. Sci. USA 74 (2): 560–564 (Feb. 1977).

McConnell, H.M. et al., "The Cytosensor Microphysiometer: Biological Applications of Silicon Technology", Science 257: 1906–1912 (Sep. 25, 1992).

McDowell, Tarra L. et al., "A Genetic Association Between Juvenile Rheumatoid Arthritis and a Novel Interleukin–1 Polymorphism", Arthritis & Rheumatism 38(2): 221–228 (1995).

Myers, R. et al., "Detection of Single Base Substitutions by Ribonucleasse Cleavage at Mismatches in RNA: DNA Duplexes", Science 230: 1242–1246 (Dec. 13, 1985).

Myers, R. et al., "Detection of Single Base Substitutions in Total Genomic DNA," Nature 313: 495–498 (Feb. 7, 1985).

Naeve, C. et al.., "Accuracy of Automated DNA Sequencing: A Multi–Laboratory Comparison of Sequencing Results", BioTechniques 19(3):448–453 (1995).

Newman, M. et al., "Genetic Risk for Severe Periodontal Disease", Compendium of Continuing Education in Dentistry 18:881–891 (Sep. 1997).

Nickerson, D. et al., "Automated DNA Diagnostics using and ELISA–based Oligonucleotide Ligation Assay", Proc. Natl. Acad, Sci. USA 87: 8923–8927 (Nov. 1990).

Nicklin, M. et al., "A Physical Map of the Region Encompassing the Human Interleukin–1α, Interleukin–1β, and Interleukin–1 Receptor Antagonist Genes", Genomics 19:382–384 (1994).

Nothwang, H. et al., "Molecular Cloning of the Interleukin–1 Gene Cluster: Construction of an Integrated YAC/PAC Contig and a Partial Transciptional Map in the Region of Chromosome 2q13", Genomics 41:370–378 (1997).

Nyrén, P. et al., "Solid Phase DNA Minisequencing by an Enzymatic Luminometric Inorganic Pyrophosphate Detection Assay", Analytical Biochemistry 208: 171–175 (1993).

O'Gorman, S. et al., "Recombinase–Mediated Gene Activation and Site–Specific Integration in Mammalian Cells", Science 251; 1351–1355 (Mar. 15, 1991).

Orban, P. et al., "Tissue–and Site–Specific DNA Recombination in Transgenic Mice", Proc. Natl. Acad. Sci USA 89: 6861–6865 (Aug. 1992).

Orita, M. et al., "Detection of Polymorphisms of Human DNA by Gel electorphoresis as Single–Strand Conformation Polymorphisms", Proc. Natl. Acad. Sci. USA 86: 2766–2770 (Apr. 1989).

Pociot, F. et al., "A Taq1 Polymorphism in the Human Interleukin1–β (IL–1β) Gene Correlates with IL–1 β Secretion in vitro", European Journal of Clinical Investigation 22:296–402 (1992).

Saiki, R. et al., "Analysis of Enzymatically Amplified β–globin and HLA–DQα DNA with Allele–specific Oligonucleotide Probes", Nature 324: 163166 (Nov. 13, 1986).

Saiki, R. et al., "Genetic Analysis of Amplified DNA with Immobilization Sequence–Specific Oligonucleotide Probes", Proc. Natl. Acad. Sci. USA 86:6230–6234 (Aug. 1989).

Saleeba, J. and Cotton, R., "Chemical Cleavage of Mismatch to Detect Mutations", Methods in Enzymology 217:286–295 (1993).

Sanger, F. et al., "DNA Sequencing with Chain–Terminating Inhibitors", Proc. Natl. Acad. Sci. 14(12):5463–5467 (Dec. 1977).

Stewart, C. et al., "Expression of Retroviral Vectors in Transgenic Mice Obtained by Emryo Infection", EMBO-Journal 6(2):383–388 (1987).

Sokolov, B., "Primer Extension Technique for the Detection of single Nucleotide in Genomic DNA", Nucleic Acids Research 18(2):3671 (1989).

Syvänen, A. et al., "Identification of Individuals by Analysis of Biallelic DNA Markers, Using PCR and Solid–Phase Minisequencing", Am. J. Hum. Genet. 52:46–59 (1993).

Tarlow, J. et al., "Severtiy of Alopecia Areata is Associated with a Polymorphism in the Interleukin–1 Receptor Antagonist Gene", Journal of Investigative Dermatology 103(3): 387–390 (Sep. 1994).

Tobe, V. et al., "Single-well Genotyping of Diallelic Sequence Variations by a Two-color ELISA-based Oligonucleotide Ligation Assay", Nucleic Acids research 24(19): 3728–3732 (1996).

Van der Luijt, R. et al., "Rapid Detection of Translation-Terminating Mutations at the Adenomatous Polyposis Coli (APC) Gene by Direct Protein Truncation Test", Genomics 20: 1–4 (1994).

Van der Putten, H. et al., "Efficient Insertion of Genes into the Mouse Germ Line via Retroviral vectors", Proc. Natl. Acad. Sci. 82: 6148–6152 (Sep. 1985).

Bailly et al.; "Genetic Polymorphism of Human Interleukin–1α", Eur. J. Immunol., 23: 1240–1245, (1993).

Cox et al.;"An Analysis of Linkage Disequilibrium in the Inerleukin–1 Gene Cluster, Using a Novel Grouping Method for Multiallelic Markers", Am. J. Hum. Genet. 62: 1180–1188, (1998).

Hurme and Santtila; "IL–1 Receptor Antagonist (IL–1Ra) Plasma Levels are Co–ordinately Regulated by Both IL–1Ra and Il–1β", Eur. J. Immunol. 28:2598–2602, (1998).

Kimble et al.; "Interleukin–1 Receptor Antagonist Decreases Bone Loss and Bone Resorption in Ovariectomized Rats", J. Clin. Invest. 93: 1959–1967, (May 1994).

Partial International Search Report, Mailed on Apr. 19, 2001 and Received on Apr. 24, 2001.

International Search Report Completed on Apr. 4, 2001 and Mailed on Jul. 12, 2001.

* cited by examiner

DIAGNOSTICS AND THERAPEUTICS FOR OSTEOPOROSIS

This application claims the benefit of provisional application No. 60/151,460, filed Aug. 30, 1999.

BACKGROUND OF THE INVENTION

Osteoporosis

In 1993, osteoporosis was identified as "one of the leading diseases of women" by Bernadine Healy, MD, then director of the National Institutes of Health. Complications following osteoporosis fractures are the fourth leading cause of death for women over the age of 65, following heart disease, cancer and stroke. It is the leading cause of disability in the United States and the most common cause of hip fracture.

Twenty-five million Americans suffer from osteoporosis, of which 85% are women. Type 1 osteoporosis, which is postmenopausal osteoporosis stemming from loss of estrogen, affects more than half of all women over 65 and has been detected in as many as 90 percent of women over age 75. Type II or senile osteoporosis which is strictly age related, affects both men and women usually over the age of seventy. Type III, the newest classification affecting both sexes, is drug-induced, for example, by long-term steroid therapy, known to accelerate bone loss. Patient groups that receive long term steroid therapy include asthmatics (7 million over the age of 18 in the United States) as well a patients with rheumatoid arthritis or other autoimmune diseases. Type IV is caused by an underlying disease such as rheumatoid arthritis (prevalence of 1–2% in the population).

Osteoporosis is responsible for a majority of the 1.5 million bone fractures each year leading to disabilities costing 10 billion dollars in medical, social and nursing-home costs. Even in the best hands, 40% of patients 65 years of age or older will not survive two years following a hip fracture.

In 1991, one in three American women were 50 years or older. The baby boom generation will begin to enter this age group in 1996. Because the average woman lives some thirty years after menopause, with present trends, osteoporosis threatens to be one of the biggest health threats of modern times.

Lifestyle can be a factor in onset of osteoporosis and in particular can be an important factor in building and maintaining healthy bone mass to prevent osteoporosis. Currently, persons under 65 are more likely than their parents to have had a sedentary lifestyle, bad eating habits, increased alcohol and caffeine intake, and a history of greater medication associated with bone loss. It is also clear that there is a genetic predisposition to the development of osteoporosis (see WO 94/03633 for a discussion of genetic factors in osteoporosis, which is herein incorporated by reference).

It would therefore be useful to be able to identify early those individuals at greatest risk for developing osteoporosis so that the individual can be counseled to make appropriate life style changes or institute other therapeutic interventions. For example, calcium supplements and exercise have been shown to be valuable preventive factors if used during a critical early age window. Hormone replacement therapy (HRT) has also been used successfully to combat osteoporosis occurring after menopause. HRT may be of greatest benefit if used early in the disease process before major bone loss has occurred. Since HRT has potentially serious side-effects, it would be useful for women to known their personal risk level for osteoporosis when making decisions about the use of HRT versus other interventions aimed at reducing the risk of developing osteoporosis.

The following published patent applications describe a variety of methods for diagnosing, monitoring and/or treating osteoporosis: WO 94/20615, WO 95/01995, WO 94/14844, EP93113604, WO/8809457, WO93/11149 and WO/9403633. The following references describe the association of various IL-1 gene polymorphisms in osteoporosis: U.S. Pat. No. 5,698,399; Eastell, R. et al., (1998) *Bone* 23 (5S): S375; Eastell, R. et al. and Keen, R W et al., (1998) *Bone* 23: 367–371.

Genetics of the IL-1 Gene Cluster

The IL-1 gene cluster is on the long arm of chromosome 2 (2q13) and contains at least the genes for IL-1α (IL-1A), IL-1α (IL-1B), and the IL-1 receptor antagonist (IL-1RN), within a region of 430 Kb (Nicklin, et al. (1994) Genomics, 19: 382–4). The agonist molecules, IL-1α and IL-1β, have potent pro-inflammatory activity and are at the head of many inflammatory cascades. Their actions, often via the induction of other cytokines such as IL-6 and IL-8, lead to activation and recruitment of leukocytes into damaged tissue, local production of vasoactive agents, fever response in the brain and hepatic acute phase response. All three IL-1 molecules bind to type I and to type II IL-1 receptors, but only the type I receptor transduces a signal to the interior of the cell. In contrast, the type II receptor is shed from the cell membrane and acts as a decoy receptor. The receptor antagonist and the type II receptor, therefore, are both anti-inflammatory in their actions.

Inappropriate production of IL-1 plays a central role in the pathology of many autoimmune and inflammatory diseases, including rheumatoid arthritis, inflammatory bowel disorder, psoriasis, and the like. In addition, there are stable inter-individual differences in the rates of production of IL-1, and some of this variation may be accounted for by genetic differences at IL-1 gene loci. Thus, the IL-1 genes are reasonable candidates for determining part of the genetic susceptibility to inflammatory diseases, most of which have a multifactorial etiology with a polygenic component.

Certain alleles from the IL-1 gene cluster are known to be associated with particular disease states. For example, IL-1RN (VNTR) allele 2 (U.S. Pat. No. 5,698,399) and IL-1RN (VNTR) allele 1 (Keen R W et al., (1998) *Bone* 23:367–371) have been reported to be associated with osteoporosis. Further IL-1RN (VNTR) allele 2 has been reported to be associated with nephropathy in diabetes mellitus (Blakemore, et al. (1996) Hum. Genet. 97(3): 369–74), alopecia areata (Cork, et al., (1995) J. Invest. Dermatol. 104(5 Supp.): 15S–16S; Cork et al. (1 996) Dermatol Clin 14: 671–8), Graves disease (Blakemore, et al. (1995) J. Clin. Endocrinol. 80(1): 111–5), systemic lupus erythematosus (Blakemore, et al. (1994) Arthritis Rheum. 37: 1380–85), lichen sclerosis (Clay, et al. (1994) Hum. Genet. 94: 407–10), and ulcerative colitis (Mansfield, et al. (1994) Gastoenterol. 106(3): 637–42)).

In addition, the IL-1A allele 2 from marker −889 and IL-1B (TaqI) allele 2 from marker +3954 have been found to be associated with periodontal disease (U.S. Pat. No. 5,686,246; Kornman and diGiovine (1998) Ann Periodont 3: 327–38; Hart and Kornman (1997) Periodontol 2000 14: 202–15; Newman (1997) Compend Contin Educ Dent 18: 881–4; Kornman et al. (1997) J. Clin Periodontol 24: 72–77). The IL-1A allele 2 from marker −889 has also been found to be associated with juvenile chronic arthritis, particularly chronic iridocyclitis (McDowell, et al. (1995) Arthritis Rheum. 38: 221–28). The IL-1B (TaqI) allele 2 from marker +3954 of IL-1B has also been found to be associated with psoriasis and insulin dependent diabetes in DR3/4 patients (di Giovine, et al. (1995) Cytokine 7: 606; Pociot, et al. (1992) Eur J. Clin. Invest. 22: 396–402). Additionally, the IL-1RN (VNTR) allele 1 has been found to be associated with diabetic retinopathy (see U.S. Ser. No. 09/037,472, and PCT/GB97/02790). Furthermore allele 2 of IL-1RN (VNTR) has been found to be associated with ulcerative colitis in Caucasian populations from North America and Europe (Mansfield, J. et al., (1994) Gastroenterology 106: 637–42). Interestingly, this association is particularly strong within populations of ethnically related Ashkenazi Jews (PCT WO97/25445).

Genotype Screening

Traditional methods for the screening of heritable diseases have depended on either the identification of abnormal gene products (e.g., sickle cell anemia) or an abnormal phenotype (e.g., mental retardation). These methods are of limited utility for heritable diseases with late onset and no easily identifiable phenotypes such as, for example, vascular disease. With the development of simple and inexpensive genetic screening methodology, it is now possible to identify polymorphisms that indicate a propensity to develop disease, even when the disease is of polygenic origin. The number of diseases that can be screened by molecular biological methods continues to grow with increased understanding of the genetic basis of multifactorial disorders.

Genetic screening (also called genotyping or molecular screening), can be broadly defined as testing to determine if a patient has mutations (alleles or polymorphisms) that either cause a disease state or are "linked" to the mutation causing a disease state. Linkage refers to the phenomenon th DNA sequences which are close together in the genome have a tendency to be inherited together. Two sequences may be linked because of some selective advantage of co-inheritance. More typically, however, two polymorphic sequences are co-inherited because of the relative infrequency with which meiotic recombination events occur within the region between the two polymorphisms. The co-inherited polymorphic alleles are said to be in linkage disequilibrium with one another because, in a given human population, they tend to either both occur together or else not occur at all in any particular member of the population. Indeed, where multiple polymorphisms in a given chromosomal region are found to be in linkage disequilibrium with one another, they define a quasi-stable genetic "haplotype." In contrast, recombination events occurring between two polymorphic loci cause them to become separated onto distinct homologous chromosomes. If meiotic recombination between two physically linked polymorphisms occurs frequently enough, the two polymorphisms will appear to segregate independently and are said to be in linkage equilibrium.

While the frequency of meiotic recombination between two markers is generally proportional to the physical distance between them on the chromosome, the occurrence of "hot spots" as well as regions of repressed chromosomal recombination can result in discrepancies between the physical and recombinational distance between two markers. Thus, in certain chromosomal regions, multiple polymorphic loci spanning a broad chromosomal domain may be in linkage disequilibrium with one another, and thereby define a broad-spanning genetic haplotype. Furthermore, where a disease-causing mutation is found within or in linkage with this haplotype, one or more polymorphic alleles of the haplotype can be used as a diagnostic or prognostic indicator of the likelihood of developing the disease. This association between otherwise benign polymorphisms and a disease-causing polymorphism occurs if the disease mutation arose in the recent past, so that sufficient time has not elapsed for equilibrium to be achieved through recombination events. Therefore identification of a human haplotype which spans or is linked to a disease-causing mutational change, serves as a predictive measure of an individual's likelihood of having inherited that disease-causing mutation. Importantly, such prognostic or diagnostic procedures can be utilized without necessitating the identification and isolation of the actual disease-causing lesion. This is significant because the precise determination of the molecular defect involved in a disease process can be difficult and laborious, especially in the case of multifactorial diseases such as inflammatory disorders.

Indeed, the statistical correlation between an inflammatory disorder and an IL-1 polymorphism does not necessarily indicate that the polymorphism directly causes the disorder. Rather the correlated polymorphism may be a benign allelic variant which is linked to (i.e. in linkage disequilibrium with) a disorder-causing mutation which has occurred in the recent human evolutionary past, so that sufficient time has not elapsed for equilibrium to be achieved through recombination events in the intervening chromosomal segment. Thus, for the purposes of diagnostic and prognostic assays for a particular disease, detection of a polymorphic allele associated with that disease can be utilized without consideration of whether the polymorphism is directly involved in the etiology of the disease. Furthermore, where a given benign polymorphic locus is in linkage disequilibrium with an apparent disease-causing polymorphic locus, still other polymorphic loci which are in linkage disequilibrium with the benign polymorphic locus are also likely to be in linkage disequilibrium with the disease-causing polymorphic locus. Thus these other polymorphic loci will also be prognostic or diagnostic of the likelihood of having inherited the disease-causing polymorphic locus. Indeed, a broad-spanning human haplotype (describing the typical pattern of co-inheritance of alleles of a set of linked polymorphic markers) can be targeted for diagnostic purposes once an association has been drawn between a particular disease or condition and a corresponding human haplotype. Thus, the determination of an individual's likelihood for developing a particular disease of condition can be made by characterizing one or more disease-associated polymorphic alleles (or even one or more disease-associated haplotypes) without necessarily determining or characterizing the causative genetic variation.

SUMMARY OF THE INVENTION

In one aspect, the present invention provides novel methods and kits for determining whether a female subject is predisposed to developing osteoporosis, comprising identifying the IL-1 haplotype pattern of the female, wherein the presence of haplotype pattern 1 indicates that the female is susceptible to larger bone loss and/or increased risk of fracture during the early menopausal years and the presence of haplotype pattern 2 indicates that the female is susceptible to larger bone loss and/or increased risk of fracture during post-menopause.

IL-1 haplotype patterns can be identified by detecting any of the component alleles using any of a variety of available techniques, including: 1) performing a hybridization reaction between a nucleic acid sample and a probe that is capable of hybridizing to the allele; 2) sequencing at least a portion of the allele; or 3) determining the electrophoretic mobility of the allele or fragments thereof (e.g., fragments generated by endonuclease digestion). The allele can optionally be subjected to an amplification step prior to performance of the detection step. Preferred amplification methods are selected from the group consisting of: the polymerase chain reaction (PCR), the ligase chain reaction (LCR), strand displacement amplification (SDA), cloning, and variations of the above (e.g. RT-PCR and allele specific amplification). Oligonucleotides necessary for amplification may be selected, for example, from within the IL-1 gene loci, either flanking the marker of interest (as required for PCR amplification) or directly overlapping the marker (as in ASO hybridization). In a particularly preferred embodiment, the sample is hybridized with a set of primers, which hybridize 5' and 3' in a sense or antisense sequence to the vascular disease associated allele, and is subjected to a PCR amplification.

An allele may also be detected indirectly, e.g. by analyzing the protein product encoded by the DNA. For example, where the marker in question results in the translation of a mutant protein, the protein can be detected by any of a variety of protein detection methods. Such methods include immunodetection and biochemical tests, such as size fractionation, where the protein has a change in apparent molecular weight either through truncation, elongation, altered folding or altered post-translational modifications.

In another aspect, the invention features kits for performing the above-described assays. The kit can include a nucleic acid sample collection means and a means for determining whether a subject carries at least one allele comprising an IL-1 haplotype. The kit may also contain a control sample either positive or negative or a standard and/or an algorithmic device for assessing the results and additional reagents and components including: DNA amplification reagents, DNA polymerase, nucleic acid amplification reagents, restrictive enzymes, buffers, a nucleic acid sampling device, DNA purification device, deoxynucleotides, oligonucleotides (e.g. probes and primers) etc.

As described above, the control may be a positive or negative control. Further, the control sample may contain the positive (or negative) products of the allele detection technique employed. For example, where the allele detection technique is PCR amplification, followed by size fractionation, the control sample may comprise DNA fragments of the appropriate size. Likewise, where the allele detection technique involves detection of a mutated protein, the control sample may comprise a sample of mutated protein. However, it is preferred that the control sample comprises the material to be tested. For example, the controls may be a sample of genomic DNA or a cloned portion of the IL-1 gene cluster. Preferably, however, the control sample is a highly purified sample of genomic DNA where the sample to be tested is genomic DNA.

The oligonucleotides present in said kit may be used for amplification of the region of interest or for direct allele specific oligonucleotide (ASO) hybridization to the markers in question. Thus, the oligonucleotides may either flank the marker of interest (as required for PCR amplification) or directly overlap the marker (as in ASO hybridization).

Information obtained using the assays and kits described herein (alone or in conjunction with information on another genetic defect or environmental factor, which contributes to osteoporosis) is useful for determining whether a non-symptomatic subject has or is likely to develop the particular disease or condition. In addition, the information can allow a more customized approach to preventing the onset or progression of the disease or condition. For example, this information can enable a clinician to more effectively prescribe a therapy that will address the molecular basis of the disease or condition.

In yet a further aspect, the invention features methods for treating or preventing osteoporosis in a subject by administering to the subject an appropriate therapeutic of the invention. In still another aspect, the invention provides in vitro or in vivo assays for screening test compounds to identify therapeutics for treating or preventing the development of osteoporosis. In one embodiment, the assay comprises contacting a cell transfected with a causative mutation that is operably linked to an appropriate promoter with a test compound and determining the level of expression of a protein in the cell in the presence and in the absence of the test compound. In a preferred embodiment, the causative mutation results in decreased production of IL-1 receptor antagonist, and increased production of the IL-1 receptor antagonist in the presence of the test compound indicates that the compound is an agonist of IL-1 receptor antagonist activity. In another preferred embodiment, the causative mutation results in increased production of IL-1α or IL-1β, and decreased production of IL-1α or IL-1β in the presence of the test compound indicates that the compound is an antagonist of IL-1α or IL-1β activity. In another embodiment, the invention features transgenic non-human animals and their use in identifying antagonists of IL-1α or IL-1β activity or agonists of IL-1Ra activity.

Other embodiments and advantages of the invention are set forth in the following detailed description and claims.

DETAILED DESCRIPTION OF THE INVENTION

Definitions

Figure 1:
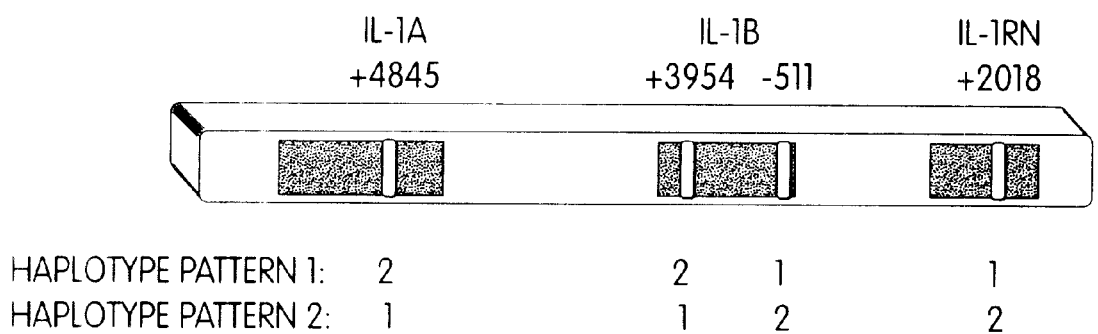
FIG. 1 shows two different genetic haplotype patterns.

For convenience, the meaning of certain terms and phrases employed in the specification, examples, and appended claims is provided below.

The term "allele" refers to the different sequence variants found at different polymorphic regions. For example, IL-1RN (VNTR) has at least five different alleles. The sequence variants may be single or multiple base changes, including without limitation insertions, deletions, or substitutions, or may be a variable number of sequence repeats.

The term "allelic pattern" refers to the identity of an allele or alleles at one or more polymorphic regions. For example, an allelic pattern may consist of a single allele at a polymorphic site, as for IL-1RN (VNTR) allele 1, which is an allelic pattern having at least one copy of IL-1RN allele 1 at the VNTR of the IL-1RN gene loci. Alternatively, an allelic pattern may consist of either a homozygous or heterozygous state at a single polymorphic site. For example, IL1-RN (VNTR) allele 2,2 is an allelic pattern in which there are two copies of the second allele at the VNTR marker of IL-1RN that corresponds to the homozygous IL-RN (VNTR) allele 2 state. Alternatively, an allelic pattern may consist of the identity of alleles at more than one polymorphic site.

The term "antibody " as used herein is intended to refer to a binding agent including a whole antibody or a binding fragment thereof which is specifically reactive with an IL-1 polypeptide. Antibodies can be fragmented using conventional techniques and the fragments screened for utility in the same manner as described above for whole antibodies. For example, F(ab)$_2$ fragments can be generated by treating an antibody with pepsin. The resulting F(ab)$_2$ fragment can be treated to reduce disulfide bridges to produce Fab fragments. The antibody of the present invention is further intended to include bispecific, single-chain, and chimeric and humanized molecules having affinity for an IL-1B polypeptide conferred by at least one CDR region of the antibody.

"Biological activity" or "bioactivity" or "activity" or "biological function", which are used interchangeably, for the purposes herein means an effector or antigenic function that is directly or indirectly performed by an IL-1 polypeptide (whether in its native or denatured conformation), or by any subsequence thereof. Biological activities include binding to a target peptide, e.g., an IL-1 receptor. An IL-1 bioactivity can be modulated by directly affecting an IL-1 polypeptide. Alternatively, an IL-1 bioactivity can be modulated by modulating the level of an IL-1 polypeptide, such as by modulating expression of an IL-1 gene.

As used herein the term "bioactive fragment of an IL-1 polypeptide" refers to a fragment of a full-length IL-1 polypeptide, wherein the fragment specifically mimics or antagonizes the activity of a wild-type IL-1 polypeptide. The bioactive fragment preferably is a fragment capable of interacting with an interleukin receptor.

The term "an aberrant activity", as applied to an activity of a polypeptide such as IL-1, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide. A cell can have an aberrant IL-1 activity due to overexpression or underexpression of an IL-1 locus gene encoding an IL-1 locus polypeptide.

"Cells", "host cells" or "recombinant host cells" are terms used interchangeably herein to refer not only to the particular subject cell, but to the progeny or potential progeny of such a cell. Because certain modifications may occur in succeeding generations due to either mutation or environmental influences, such progeny may not, in fact be identical to the parent cell, but are still included within the scope of the term as used herein.

A "chimera," "mosaic," "chimeric mammal" and the like, refers to a transgenic mammal with a knock-out or knock-in construct in at least some of its genome-containing cells.

The terms "control" or "control sample" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested. For example, the controls may be a sample of genomic DNA or a cloned portion of the IL-1 gene cluster. However, where the sample to be tested is genomic DNA, the control sample is preferably a highly purified sample of genomic DNA.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

The term "haplotype" as used herein is intended to refer to a set of alleles that are inherited together as a group (are in linkage disequilibrium) at statistically significant levels ($p_{corr}$<0.05). As used herein, the phrase "an IL-1 haplotype" refers to a haplotype in the IL-1 loci. An IL-1 inflammatory or proinflammatory haplotype refers to a haplotype that is indicative of increased agonist and/or decreased antagonist activities.

The terms "IL-1 gene cluster" and "IL-1 loci" as used herein include all the nucleic acid at or near the 2q13 region of chromosome 2, including at least the IL-1A, IL-1B and IL-1RN genes and any other linked sequences. (Nicklin et al., *Genomics* 19: 382–84, 1994). The terms "IL-1A", "IL-1B", and "IL-1RN" as used herein refer to the genes coding for IL-1, IL-1, and IL-1 receptor antagonist, respectively. The gene accession number for IL-1A, IL-1B, and IL-1RN are X03833, X04500, and X64532, respectively.

"IL-1 functional mutation" refers to a mutation within the IL-1 gene cluster that results in an altered phenotype (i.e. effects the function of an IL-1 gene or protein). Examples include: IL-1A(+4845) allele 2, IL-1B (+3954) allele 2, IL-1B (+6912) allele 2 and IL-1RN (+2018) allele 2.

"IL-1X (Z) allele Y" refers to a particular allelic form, designated Y, occurring at an IL-1 locus polymorphic site in gene X, wherein X is IL-1A, B, or RN and positioned at or near nucleotide Z, wherein nucleotide Z is numbered relative to the major transcriptional start site, which is nucleotide +1, of the particular IL-1 gene X. As further used herein, the term "IL-1X allele (Z)" refers to all alleles of an IL-1 polymorphic site in gene X positioned at or near nucleotide Z. For example, the term "IL-1RN (+2018) allele" refers to alternative forms of the IL-1RN gene at marker +2018. "IL-1RN (+2018) allele 1" refers to a form of the IL-1RN gene which contains a cytosine (C) at position +2018 of the sense strand. Clay et al., *Hum. Genet.* 97:723–26, 1996. "IL-1RN (+2018) allele 2" refers to a form of the IL-1RN gene which contains a thymine (T) at position +2018 of the plus strand. When a subject has two identical IL-1RN alleles, the subject is said to be homozygous, or to have the homozygous state. When a subject has two different IL-1RN alleles, the subject is said to be heterozygous, or to have the heterozygous state. The term "IL-1RN (+2018) allele 2,2" refers to the homozygous IL-1RN (+2018) allele 2 state. Conversely, the term "IL-1RN (+2018) allele 1,1" refers to the homozygous IL-1RN (+2018) allele 1 state. The term "IL-1RN (+2018) allele 1,2" refers to the heterozygous allele 1 and 2 state.

"IL-1 related" as used herein is meant to include all genes related to the human IL-1 locus genes on human chromosome 2 (2q 12–14). These include IL-1 genes of the human IL-1 gene cluster located at chromosome 2 (2q 13–14) which include: the IL-1A gene which encodes interleukin- 1α, the IL-1B gene which encodes interleukin-1β, and the IL-1RN (or IL-1ra) gene which encodes the interleukin-1 receptor antagonist. Furthermore these IL-1 related genes include the type I and type II human IL-1 receptor genes located on human chromosome 2 (2q12) and their mouse homologs located on mouse chromosome 1 at position 19.5 cM. Interleukin-1α, interleukin-1β, and interleukin-1RN are related in so much as they all bind to IL-1 type I receptors, however only interleukin-1α and interleukin-1β are agonist ligands which activate IL-1 type I receptors, while interleukin-1RN is a naturally occurring antagonist ligand. Where the term "IL-1" is used in reference to a gene product or polypeptide, it is meant to refer to all gene products encoded by the interleukin-1 locus on human chromosome 2 (2q 12–14) and their corresponding homologs from other species or functional variants thereof. The term IL-1 thus includes secreted polypeptides which promote an inflammatory response, such as IL-1α and IL-1β, as well as a secreted polypeptide which antagonize inflammatory responses, such as IL-1 receptor antagonist and the IL-1 type II (decoy) receptor.

An "IL-1 receptor" or "IL-1R" refers to various cell membrane bound protein receptors capable of binding to and/or transducing a signal from an IL-1 locus-encoded ligand. The term applies to any of the proteins which are capable of binding interleukin-1 (IL-1) molecules and, in their native configuration as mammalian plasma membrane proteins, presumably play a role in transducing the signal provided by IL-1 to a cell. As used herein, the term includes analogs of native proteins with IL-1-binding or signal transducing activity. Examples include the human and murine IL-1 receptors described in U.S. Pat. No. 4,968,607. The term "IL-1 nucleic acid" refers to a nucleic acid encoding an IL-1 protein.

Figure 2:
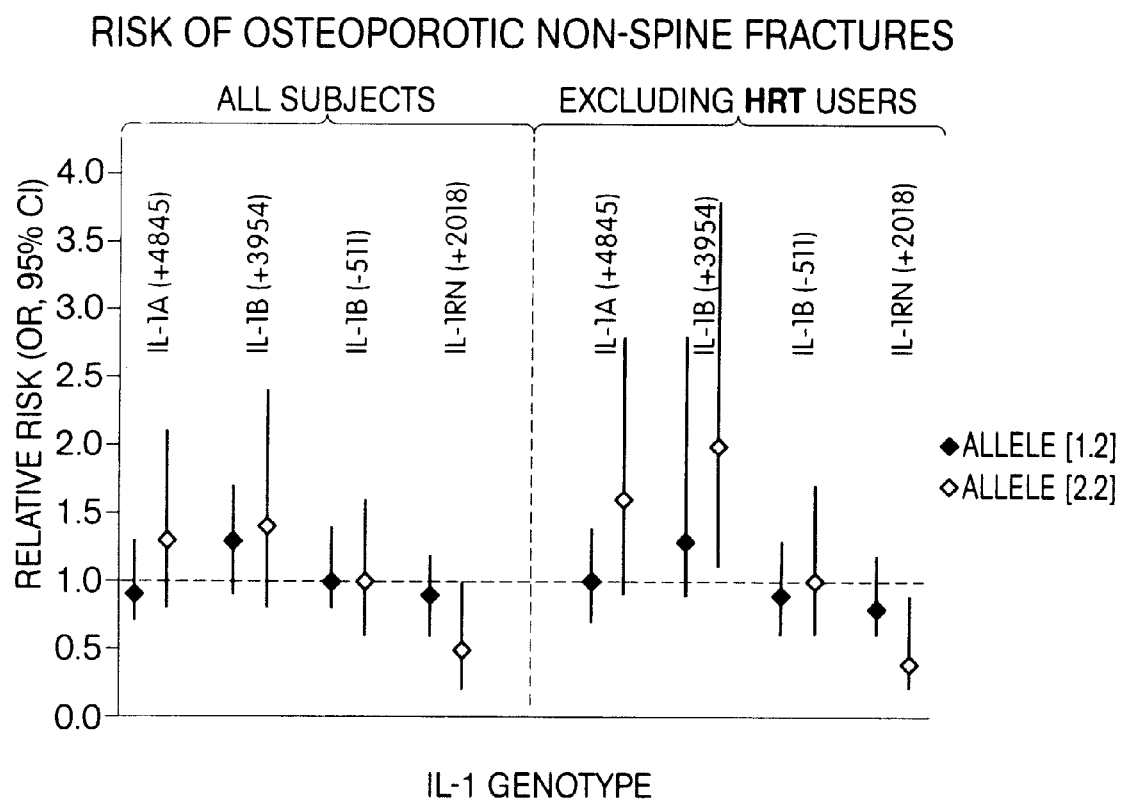
FIG. 2 is a graph showing the risk of osteoporotic non-spine fractures.
Figure 3:
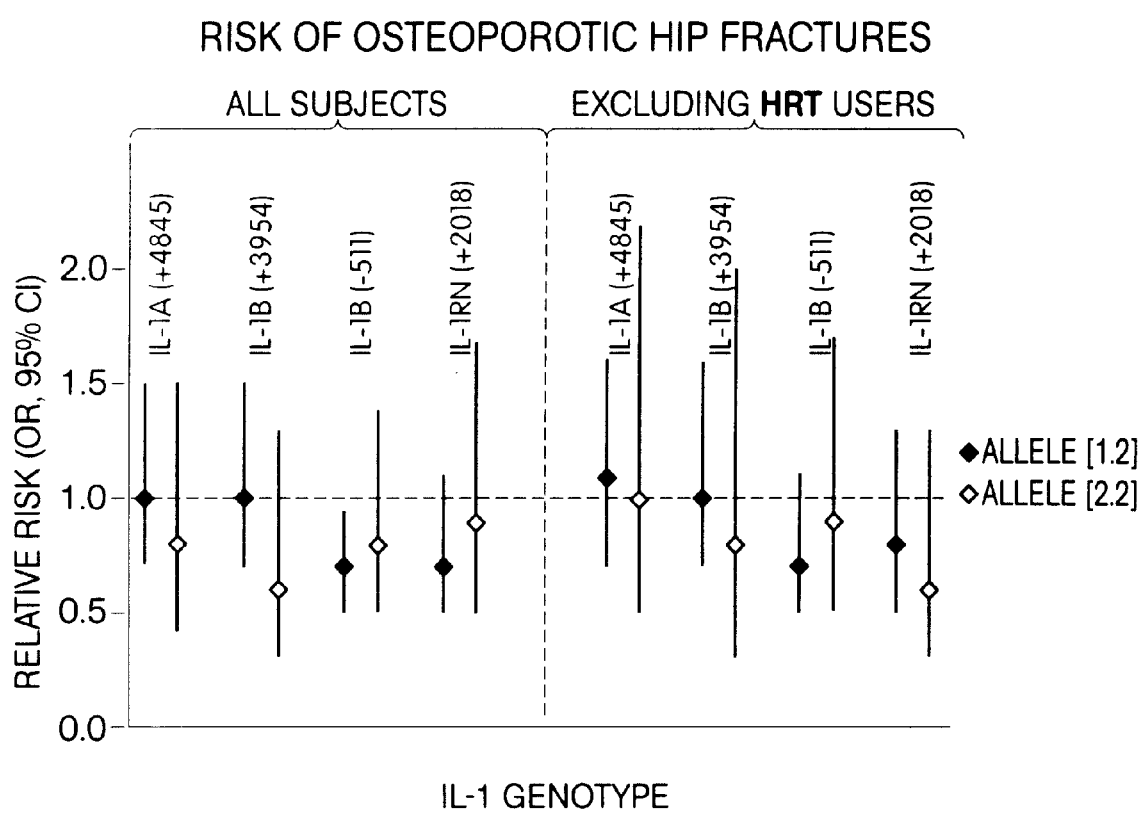
FIG. 3 is a graph showing the risk of osteoporotic hip fractures

An "IL-1 polypeptide" and "IL-1 protein" are intended to encompass polypeptides comprising the amino acid sequence encoded by the IL-1 genomic DNA sequences shown in FIGS. 1, 2, and 3, or fragments thereof, and homologs thereof and include agonist and antagonist polypeptides.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

The term "interact" as used herein is meant to include detectable relationships or associations (e.g. biochemical interactions) between molecules, such as interactions between protein-protein, protein-nucleic acid, nucleic acid-nucleic acid and protein-small molecule or nucleic acid-small molecule in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject IL-1 polypeptides preferably includes no more than 10 kilobases (kb) of nucleic acid sequence which naturally immediately flanks the IL-1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

A "knock-in" transgenic animal refers to an animal that has had a modified gene introduced into its genome and the modified gene can be of exogenous or endogenous origin.

A "knock-out" transgenic animal refers to an animal in which there is partial or complete suppression of the expression of an endogenous gene (e.g, based on deletion of at least a portion of the gene, replacement of at least a portion of the gene with a second sequence, introduction of stop codons, the mutation of bases encoding critical amino acids, or the removal of an intron junction, etc.).

A "knock-out construct" refers to a nucleic acid sequence that can be used to decrease or suppress expression of a protein encoded by endogenous DNA sequences in a cell. In a simple example, the knock-out construct is comprised of a gene, such as the IL-1RN gene, with a deletion in a critical portion of the gene, so that active protein cannot be expressed therefrom. Alternatively, a number of termination codons can be added to the native gene to cause early termination of the protein or an intron junction can be inactivated. In a typical knock-out construct, some portion of the gene is replaced with a selectable marker (such as the neo gene) so that the gene can be represented as follows: IL-1RN 5'/neo/IL-1RN 3', where IL-1RN5' and IL-1RN 3', refer to genomic or cDNA sequences which are, respectively, upstream and downstream relative to a portion of the IL-1RN gene and where neo refers to a neomycin resistance gene. In another knock-out construct, a second selectable marker is added in a flanking position so that the gene can be represented as: IL-1RN/neo/IL-1RN/TK, where TK is a thymidine kinase gene which can be added to either the IL-1RN5' or the IL-1RN3' sequence of the preceding construct and which further can be selected against (i.e. is a negative selectable marker) in appropriate media. This two-marker construct allows the selection of homologous recombination events, which removes the flanking TK marker, from non-homologous recombination events which typically retain the TK sequences. The gene deletion and/or replacement can be from the exons, introns, especially intron junctions, and/or the regulatory regions such as promoters.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in "linkage disequilibrium". The cause of linkage disequilibrium is often unclear. It can be due to selection for certain allele combinations or to recent admixture of genetically heterogeneous populations. In addition, in the case of markers that are very tightly linked to a disease gene, an association of an allele (or group of linked alleles) with the disease gene is expected if the disease mutation occurred in the recent past, so that sufficient time has not elapsed for equilibrium to be achieved through recombination events in the specific chromosomal region. When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern. An example of linkage disequilibrium is that which occurs between the alleles at the IL-1RN (+2018) and IL-1RN (VNTR) polymorphic sites. The two alleles at IL-1RN (+2018) are 100% in linkage disequilibrium with the two most frequent alleles of IL-1RN (VNTR), which are allele 1 and allele 2.

The term "marker" refers to a sequence in the genome that is known to vary among individuals. For example, the IL-1RN gene has a marker that consists of a variable number of tandem repeats (VNTR).

A "mutated gene" or "mutation" or "functional mutation" refers to an allelic form of a gene, which is capable of altering the phenotype of a subject having the mutated gene relative to a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

A "non-human animal" of the invention includes mammals such as rodents, non-human primates, sheep, dogs, cows, goats, etc. amphibians, such a s members of the Xenopus genus, and transgenic avians (e.g. chickens, birds, etc.). The term "chimeric animal" is used herein to refer to animals in which the recombinant gene is found, or in which the recombinant gene is expressed in some but not all cells of the animal. The term "tissue-specific chimeric animal" indicates that one of the recombinant IL-1 genes is present and/or expressed or disrupted in some tissues but not others. The term "non-human mammal" refers to any member of the class Mammalia, except for humans.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs (e.g. peptide nucleic acids) and as applicable to the embodiment being described, single (sense or antisense) and double-stranded polynucleotides.

The term "osteoporosis" is defined by the World Health Organization as " . . . a systemic skeletal disease characterized by low bone mass and micro-architectural deterioration of bone tissue, with a consequent increase in bone fragility and susceptibility to fracture" (WHO Consensus Development Conference 1993). The clinical definition of osteoporosis is a condition in which the bone mineral density (BMD) or bone mineral concentration (BMC) is greater than about 2.5 standard deviations (SD) below the mean of young healthy women. Severe osteoporosis is defined as having a BMD or BMC greater than about 2.5 SD below the mean of young healthy women and the presence of one or more fragility fractures. Since bone loss is not strictly confined to specific sites, osteoporosis can manifest itself in various ways including alveolar, femoral, radial, vertebral or wrist bone loss or fracture incidence, postmenopausal bone loss, severely reduced bone mass, fracture incidence or rate of bone loss.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

The term "propensity to disease," also "predisposition" or "susceptibility" to disease or any similar phrase, means that certain alleles are hereby discovered to be associated with or predictive of a subject's incidence of developing a particular disease (e.g. a vascular disease). The alleles are thus over-represented in frequency in individuals with disease as compared to healthy individuals. Thus, these alleles can be used to predict disease even in pre-symptomatic or pre-diseased individuals.

"Small molecule" as used herein, is meant to refer to a composition, which has a molecular weight of less than about 5kD and most preferably less than about 4 kD. Small molecules can be nucleic acids, peptides, peptidomimetics, carbohydrates, lipids or other organic or inorganic molecules.

As used herein, the term "specifically hybridizes" or "specifically detects" refers to the ability of a nucleic acid molecule to hybridize to at least approximately 6 consecutive nucleotides of a sample nucleic acid.

"Transcriptional regulatory sequence" is a generic term used throughout the specification to refer to DNA sequences, such as initiation signals, enhancers, and promoters, which induce or control transcription of protein coding sequences with which they are operably linked.

As used herein, the term "transgene" means a nucleic acid sequence (encoding, e.g., one of the IL-1 polypeptides, or an antisense transcript thereto) which has been introduced into a cell. A transgene could be partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can also be present in a cell in the form of an episome. A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of an IL-1 polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and anti-sense techniques. The term is intended to include all progeny generations. Thus, the founder animal and all F1, F2, F3, and so on, progeny thereof are included.

The term "treating" as used herein is intended to encompass curing as well as ameliorating at least one symptom of a condition or disease.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

Predictive Medicine

Identifying IL-2Alleles and Haplotypes

The present invention is based at least in part, on the identification of certain alleles that have been determined to be association (to a statistically significant extent) to bone loss, fracture risk or other indicators of osteoporosis. Therefore, detection of the alleles can indicate that the subject has or is predisposed to the development of osteoporosis. However, because these alleles are in linkage disequilibrium with other alleles, the detection of such other linked alleles can also indicate that the subject has or is predisposed to the development of a particular disease or condition. For example, the 44112332 haplotype comprises the following genotype:

allele 4 of the 222/223 marker of IL-1A
allele 4 of the gz5/gz6 marker of IL-1A
allele 1 of the −889 marker of IL-1A
allele 1 of the +3954 maker of IL-1B
allele 2 of the −511 marker of IL-1B
allele 3 of the gaat.p33330 marker
allele 3 of the Y31 marker
allele 2 of +2018 of IL-1RN
allele 2 of the VNTR marker of IL-1R Three other polymorphisms in an IL-1RN alternative exon (Exon lic, which produces an intracellular form of the gene product) are also in linkage disequilibrium with allele 2 of IL-1RN (VNTR) (Clay et al., (1996) Hum Genet 97:723–26). These include: IL-1RN exon lic (1812) (GenBank:X77090 at 1812); the IL-1RN exon lic (1868) polymorphism (GenBank:X77090 at 1868); and the IL-1RN exon lic (1887) polymorphism (GenBank:X77090 at 1887). Furthermore yet another polymorphism in the promoter for the alternatively spliced intracellular form of the gene, the Pic (1731) polymorphism (GenBank:X77090 at 1731), is also in linkage disequilibrium with allele 2 of the IL-1RN (VNTR) polymorphic locus. For each of these polymorphic loci, the allele 2 sequence variant has been determined to be in linkage disequilibrium with allele 2 of the IL-1RN (VNTR) locus (Clay et al., (1996) Hum Genet 97:723–26).

The 33221461 haplotype comprises the following genotype:

allele 3 of the 222/223 marker of IL-1A
allele 3 of the gz5/gz6 marker of IL-1A
allele 2 of the −889 marker of IL-1A
allele 2 of the +3954 marker of IL-1B
allele 1 of the −511 marker of IL-1B
allele 4 of the gaat.p33330 marker
allele 6 of the Y31 marker
allele 1 of +2018 of IL-1RN
allele 1 of the VNTR marker of IL-1RN Individuals with the 44112332 haplotype are typically overproducers of both IL-1α and IL-1β proteins, upon stimulation. In contrast, individuals with the 33221461 haplotype are typically underproducers of IL-1ra. Each haplotype results in a net proinflammatory response. Each allele within a haplotype may have an effect, as well as a composite genotype effect. In addition, particular diseases may be associated with both haplotype patterns.

In addition to the allelic patterns described above, as described herein, one of skill in the art can readily identify other alleles (including polymorphisms and mutations) that are in linkage disequilibrium with an allele associated with osteoporosis. For example, a nucleic acid sample from a first group of subjects without osteoporosis can be collected, as well as DNA from a second group of subjects with the disorder. The nucleic acid sample can then be compared to identify those alleles that are over-represented in the second group as compared with the first group, wherein such alleles are presumably associated with osteoporosis. Alternatively, alleles that are in linkage disequilibrium with an allele that is associated with osteoporosis can be identified, for example, by genotyping a large population and performing statistical analysis to determine which alleles appear more commonly together than expected. Preferably the group is chosen to be comprised of genetically related and performing statistical analysis to determine which alleles appear more commonly together than expected. Preferably the group is chosen to be comprised of genetically related individuals. Genetically related individuals include individuals from the same race, the same ethnic group, or even the same family. As the degree of genetic relatedness between a control group and a test group increases, so does the predictive value of polymorphic alleles which are ever more distantly linked to a disease-causing allele. This is because less evolutionary time has passed to allow polymorphisms which are linked along a chromosome in a founder population to redistribute through genetic crossover events. Thus race-specific, ethnic-specific, and even family-specific diagnostic genotyping assays can be developed to allow for the detection of disease alleles which arose at ever more recent times in human evolution, e.g., after divergence of the major human races, after the separation of human populations into distinct ethnic groups, and even within the recent history of a particular family line.

Linkage disequilibrium between two polymorphic markers or between one polymorphic marker and a disease-causing mutation is a meta-stable state. Absent selective pressure or the sporadic linked reoccurrence of the underlying mutational events, the polymorphisms will eventually become disassociated by chromosomal recombination events and will thereby reach linkage equilibrium through the course of human evolution. Thus, the likelihood of finding a polymorphic allele in linkage disequilibrium with a disease or condition may increase with changes in at least two factors: decreasing physical distance between the polymorphic marker and the disease-causing mutation, and decreasing number of meiotic generations available for the dissociation of the linked pair. Consideration of the latter factor suggests that, the more closely related two individuals are, the more likely they will share a common parental chromosome or chromosomal region containing the linked polymorphisms and the less likely that this linked pair will have become unlinked through meiotic cross-over events occurring each generation. As a result, the more closely related two individuals are, the more likely it is that widely spaced polymorphisms may be co-inherited. Thus, for individuals related by common race, ethnicity or family, the reliability of ever more distantly spaced polymorphic loci can be relied upon as an indicator of inheritance of a linked disease-causing mutation.

Figure 4:
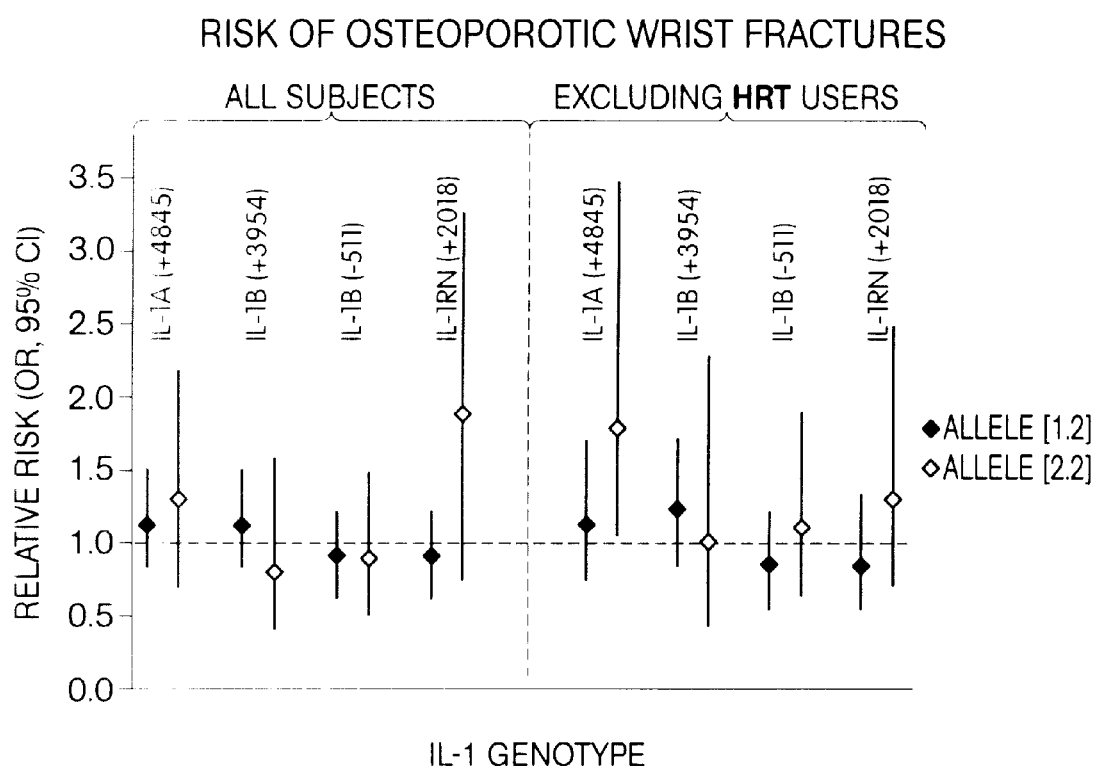
FIG. 4 is a graph showing the risk of osteoporotic wrist fractures
Figure 5:
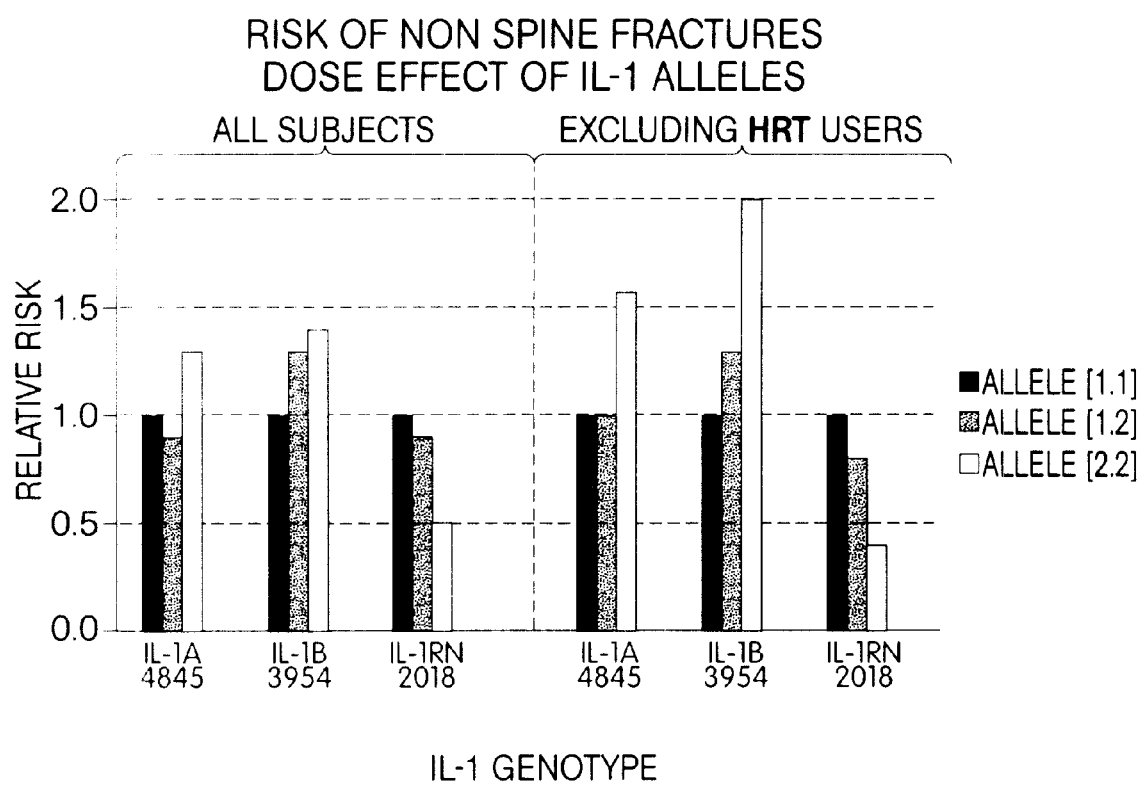
FIG. 5 is a graph showing the risk of non-spine fractures

Appropriate probes may be designed to hybridize to a specific gene of the IL-1 locus, such as IL-1A, IL-1B or IL-1RN or a related gene. These genomic DNA sequences are shown in FIGS. 3, 4 and 5, respectively, and further correspond to SEQ ID Nos. 1, 2 and 3, respectively. Alternatively, these probes may incorporate other regions of the relevant genomic locus, including intergenic sequences. Indeed the IL-1 region of human chromosome 2 spans some 400,000 base pairs and, assuming an average of one single nucleotide polymorphism every 1,000 base pairs, includes some 400 SNPs loci alone. Yet other polymorphisms available for use with the immediate invention are obtainable from various public sources. For example, the human genome database collects intragenic SNPs, is searchable by sequence and currently contains approximately 2,700 entries (http://hgbase.interactiva.de). Also available is a human polymorphism database maintained by the Massachusetts Institute of Technology (MIT SNP database (http://www.genome.wi.mit.edu/SNP/human/index.html)). From such sources SNPs as well as other human polymorphisms may be found.

For example, examination of the IL-1 region of the human genome in any one of these databases reveals that the IL-1 locus genes are flanked by a centromere proximal polymorphic marker designated microsatellite marker AFM220ze3 at 127.4 cM (centiMorgans) (see GenBank Acc. No. Z17008) and a distal polymorphic marker designated microsatellite anchor marker AFM087xal at 127.9 cM (see GenBank Acc. No. Z16545). These human polymorphic loci are both CA dinucleotide repeat microsatellite polymorphisms, and, as such, show a high degree of heterozygosity in human populations. For example, one allele of AFM220ze3 generates a 211 bp PCR amplification product with a 5' primer of the sequence TGTACCTAAGC-CCACCCTTTAGAGC (SEQ ID No. 4) and a 3' primer of the sequence TGGCCTCCAGAAACCTCCAA (SEQ ID No. 5). Furthermore, one allele of AFM087xal generates a 177 bp PCR amplification product with a 5' primer of the sequence GCTGATATTCTGGTGGGAAA (SEQ ID No. 6) and a 3' primer of the sequence GGCAAGAG-CAAAACTCTGTC (SEQ ID No. 7). Equivalent primers corresponding to unique sequences occurring 5' and 3' to these human chromosome 2 CA dinucleotide repeat polymorphisms will be apparent to one of skill in the art. Reasonable equivalent primers include those which hybridize within about 1 kb of the designated primer, and which further are anywhere from about 17 bp to about 27 bp in length. A general guideline for designing primers for amplification of unique human chromosomal genomic sequences is that they possess a melting temperature of at least about 50° C., wherein an approximate melting temperature can be estimated using the formula $T_{melt}=[2\times(\# \text{ of A or T})+4\times(\# \text{ of G or C})]$.

A number of other human polymorphic loci occur between these two CA dinucleotide repeat polymorphisms and provide additional targets for determination of a prognostic allele in a family or other group of genetically related individuals. For example, the National Center for Biotechnology Information web site (www.ncbi.nlm.nih.gov/genemap/) lists a number of polymorphism markers in the region of the IL-1 locus and provides guidance in designing appropriate primers for amplification and analysis of these markers.

Accordingly, the nucleotide segments of the invention may be used for their ability to selectively form duplex molecules with complementary stretches of human chromosome 2 q 12–13 or cDNAs from that region or to provide primers for amplification of DNA or cDNA from this region. The design of appropriate probes for this purpose requires consideration of a number of factors. For example, fragments having a length of between 10, 15, or 18 nucleotides to about 20, or to about 30 nucleotides, will find particular utility. Longer sequences, e.g., 40, 50, 80, 90, 100, even up to full length, are even more preferred for certain embodiments. Lengths of oligonucleotides of at least about 18 to 20 nucleotides are well accepted by those of skill in the art as sufficient to allow sufficiently specific hybridization so as to be useful as a molecular probe. Furthermore, depending on the application envisioned, one will desire to employ varying conditions of hybridization to achieve varying degrees of selectivity of probe towards target sequence. For applications requiring high selectivity, one will typically desire to employ relatively stringent conditions to form the hybrids. For example, relatively low salt and/or high temperature conditions, such as provided by 0.02 M–0.15M NaCl at temperatures of about 50° C. to about 70° C. Such selective conditions may tolerate little, if any, mismatch between the probe and the template or target strand.

Other alleles or other indicia of a disorder can be detected or monitored in a subject in conjunction with detection of the alleles described above, for example, identifying vessel wall thickness (e.g. as measured by ultrasound), or whether the subject smokes, drinks is overweight, is under stress or exercises.

Detection of Alleles

Many methods are available for detecting specific alleles at human polymorphic loci. The preferred method for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. SNPs are most frequently biallelic-occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

A variety of methods are available for detecting the presence of a particular single nucleotide polymorphic allele in an individual. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

Several methods have been developed to facilitate analysis of single nucleotide polymorphisms. In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A.-C., et al., Genomics 8:684–692 (1990); Kuppuswamy, M. N. et al., Proc. Natl. Acad. Sci. (U.S.A.) 88:1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C., et al., Amer. J. Hum. Genet. 52:46–59 (1993)).

For mutations that produce premature termination of protein translation, the protein truncation test (PTT) offers an efficient diagnostic approach (Roest, et. al., (1993) *Hum. Mol. Genet.* 2:1719–2 1; van der Luijt, et. al., (1994) *Genomics* 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

Any cell type or tissue may be utilized to obtain nucleic acid samples for use in the diagnostics described herein. In a preferred embodiment, the DNA sample is obtained from a bodily fluid, e.g, blood, obtained by known techniques (e.g. venipuncture) or saliva. Alternatively, nucleic acid tests can be performed on dry samples (e.g. hair or skin). When using RNA or protein, the cells or tissues that may be utilized must express an IL-1 gene.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

A preferred detection method is allele specific hybridization using probes overlapping a region of at least one allele of an IL-1 proinflammatory haplotype and having about 5, 10, 20, 25, or 30 nucleotides around the mutation or polymorphic region. In a preferred embodiment of the invention, several probes capable of hybridizing specifically to other allelic variants involved in a restenosis are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), and Q- Beta Replicase (Lizardi, P. M. et al., 1988, Bio/Technology 6:1197).

Amplification products may be assayed in a variety of ways, including size analysis, restriction digestion followed by size analysis, detecting specific tagged oligonucleotide primers in the reaction products, allele-specific oligonucleotide (ASO) hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of an IL-1 proinflammatory haplotype under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, the allele of an IL-1 proinflammatory haplotype is identified by alterations in restriction enzyme cleavage patterns. For example, sample and control DNA is isolated, amplified (optionally), digested with one or more restriction endonucleases, and fragment length sizes are determined by gel electrophoresis.

In yet another embodiment, any of a variety- of sequencing reactions known in the art can be used to directly sequence the allele. Exemplary sequencing reactions include those based on techniques developed by Maxim and Gilbert ((1977) Proc. Natl Acad Sci USA 74:560) or Sanger (Sanger et al (1977) Proc. Nat. Acad. Sci USA 74:5463). It is also contemplated that any of a variety of automated sequencing procedures may be utilized when performing the subject assays (see, for example Biotechniques (1995) 19:448), including sequencing by mass spectrometry (see, for example PCT publication WO 94/16101; Cohen et al. (1996) Adv Chromatogr 36:127–162; and Griffin et al. (1993) Appl Biochem Biotechnol 38:147–159). It will be evident to one of skill in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) Science 230:1242). In general, the art technique of "mismatch cleavage" starts by providing heteroduplexes formed by hybridizing (labeled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) Proc. Natl Acad Sci USA 85:4397; and Saleeba et al (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes). For example, the mutY enzyme of E. coli cleaves A at G/A mismatches and the thymidine DNA glycosylase from HeLa cells cleaves T at G/T mismatches (Hsu et al. (1994) Carcinogenesis 15:1657–1662). According to an exemplary embodiment, a probe based on an allele of an IL-1 locus haplotype is hybridized to a CDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify an IL-1 locus allele. For example, single strand conformation polymorphism (SSCP) may be used to detect differences in electrophoretic mobility between mutant and wild type nucleic acids (Orita et al. (1989) Proc Natl. Acad. Sci USA 86:2766, see also Cotton (1993) Mutat Res 285:125–144; and Hayashi (1992) Genet Anal Tech Appl 9:73–79). Single-stranded DNA fragments of sample and control IL-1 locus alleles are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of alleles in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting alleles include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) Nature 324:163); Saiki et al (1989) Proc. Natl Acad. Sci USA 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) Nucleic Acids Res. 17:2437–2448) or at the extreme 3' end of one primer where, under appropriate conditions, mismatch can prevent, or reduce polymerase extension (Prossner (1993) Tibtech 1 1:238. In addition it may be desirable to introduce a novel restriction site in the region of the mutation to create cleavage-based detection (Gasparini et al (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al. ((1988) Science 241:1077–1080). The OLA protocol uses two oligonucleotides which are designed to be capable of hybridizing to abutting sequences of a single strand of a target. One of the oligonucleotides is linked to a separation marker, e.g,. biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al. (1990) Proc. Natl. Acad. Sci. USA 87:8923–27). In this method, PCR is used to achieve the exponential amplification of target DNA, which is then detected using OLA.

Several techniques based on this OLA method have been developed and can be used to detect alleles of an IL-1 locus haplotype. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Another embodiment of the invention is directed to kits for detecting a predisposition for developing a restenosis. This kit may contain one or more oligonucleotides, including 5' and 3' oligonucleotides that hybridize 5' and 3' to at least one allele of an IL-1 locus haplotype. PCR amplification oligonucleotides should hybridize between 25 and 2500 base pairs apart, preferably between about 100 and about 500 bases apart, in order to produce a PCR product of convenient size for subsequent analysis.

Particularly preferred primers for use in the diagnostic method of the invention include SEQ ID Nos. 1–6

The design of additional oligonucleotides for use in the amplification and detection of IL-1 polymorphic alleles by the method of the invention is facilitated by the availability of both updated sequence information from human chromosome 2q13—which contains the human IL-1 locus, and updated human polymorphism information available for this locus. For example, the DNA sequence for the IL-1A, IL-1B and IL-1RN is shown in FIGS. 1 (GenBank Accession No. X03833), 2 (GenBank Accession No. X04500) and 3 (GenBank Accession No. X64532) respectively. Suitable primers for the detection of a human polymorphism in these genes can be readily designed using this sequence information and standard techniques known in the art for the design and optimization of primers sequences. Optimal design of such primer sequences can be achieved, for example, by the use of commercially available primer selection programs such as Primer 2.1, Primer 3 or GeneFisher (See also, Nicklin M. H. J., Weith A. Duff G. W., "A Physical Map of the Region Encompassing the Human Interleukin-1α, interleukin-1β, and Interleukin-1 Receptor Antagonist Genes" Genomics 19: 382 (1995); Nothwang H. G., et al. "Molecular Cloning of the Interleukin-1 gene Cluster: Construction of an Integrated YAC/PAC Contig and a partial transcriptional Map in the Region of Chromosome 2q13" Genomics 41: 370 (1997); Clark, et al. (1986) Nucl. Acids. Res., 14:7897–7914 [published erratum appears in Nucleic Acids Res., 15:868 (1987) and the Genome Database (GDB) project at the URL http://www.gdb.org).

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ labeled oligonucleotides to allow ease of identification in the assays. Examples of labels which may be employed include radio-labels, enzymes, fluorescent compounds, streptavidin, avidin, biotin, magnetic moieties, metal binding moieties, antigen or antibody moieties, and the like.

The kit may, optionally, also include DNA sampling means. DNA sampling means are well known to one of skill in the art and can include, but not be limited to substrates, such as filter papers, the AmpliCard™ (University of Sheffield, Sheffield, England S10 2JF; Tarlow, J W, et al., *J. of Invest. Dermatol.* 103:387–389 (1994)) and the like; DNA purification reagents such as Nucleon™ kits, lysis buffers, proteinase solutions and the like; PCR reagents, such as 10× reaction buffers, thernostable polymerase, dNTPs, and the like; and allele detection means such as the HinfI restriction enzyme, allele specific oligonucleotides, degenerate oligonucleotide primers for nested PCR from dried blood.

Pharmacogenomics

Knowledge of the particular alleles associated with a susceptibility to developing osteoporosis, alone or in conjunction with information on other genetic defects contributing to the same condition allows a customization of the prevention or treatment in accordance with the individual's genetic profile, the goal of "pharmacogenomics". Thus, comparison of an individual's IL-1 profile to the population profile for osteoporosis, permits the selection or design of drugs or other therapeutic regimens that are expected to be safe and efficacious for a particular patient or patient population (i.e., a group of patients having the same genetic alteration).

In addition, the ability to target populations expected to show the highest clinical benefit, based on genetic profile can enable: 1) the repositioning of already marketed drugs; 2) the rescue of drug candidates whose clinical development has been discontinued as a result of safety or efficacy limitations, which are patient subgroup-specific; and 3) an accelerated and less costly development for candidate therapeutics and more optimal drug labeling (e.g. since measuring the effect of various doses of an agent on the causative mutation is useful for optimizing effective dose).

The treatment of an individual with a particular therapeutic can be monitored by determining protein (e.g. IL-1α, IL-1β, or IL-1Ra), mRNA and/or transcriptional level. Depending on the level detected, the therapeutic regimen can then be maintained or adjusted (increased or decreased in dose). In a preferred embodiment, the effectiveness of treating a subject with an agent comprises the steps of: (i) obtaining a preadministration sample from a subject prior to administration of the agent; (ii) detecting the level or amount of a protein, mRNA or genomic DNA in the preadministration sample; (iii) obtaining one or more post-administration samples from the subject; (iv) detecting the level of expression or activity of the protein, mRNA or genomic DNA in the post-administration sample; (v) comparing the level of expression or activity of the protein, mRNA or genomic DNA in the preadministration sample with the corresponding protein, mRNA or genomic DNA in the postadministration sample, respectively; and (vi) altering the administration of the agent to the subject accordingly.

Cells of a subject may also be obtained before and after administration of a therapeutic to detect the level of expression of genes other than an IL-1 gene to verify that the therapeutic does not increase or decrease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

Osteoporosis Therapeutics

Osteoporosis therapeutics refers to any agent or therapeutic regimen (including pharmaceuticals, nutraceuticals and surgical means) that prevents or postpones the development of or alleviates the symptoms of osteoporosis in the subject. The therapeutic can be a polypeptide, peptidomimetic, nucleic acid or other inorganic or organic molecule, preferably a "small molecule" including vitamins, minerals and other nutrients. Preferably the therapeutic can modulate at least one activity of an IL-1 polypeptide, e.g., interaction with a receptor, by mimicking or potentiating (agonizing) or inhibiting (antagonizing) the effects of a naturally-occurring polypeptide. An agonist can be a wild-type protein or derivative thereof having at least one bioactivity of the wild-type, e.g., receptor binding activity. An agonist can also be a compound that upregulates expression of a gene or which increases at least one bioactivity of a protein. An agonist can also be a compound which increases the interaction of a polypeptide with another molecule, e.g., a receptor. An antagonist can be a compound which inhibits or decreases the interaction between a protein and another molecule, e.g., a receptor or an agent that blocks signal transduction or post-translation processing (e.g., IL-1 converting enzyme (ICE) inhibitor). Accordingly, a preferred antagonist is a compound which inhibits or decreases binding to a receptor and thereby blocks subsequent activation of the receptor. An antagonist can also be a compound that downregulates expression of a gene or which reduces the amount of a protein present. The antagonist can be a dominant negative form of a polypeptide, e.g., a form of a polypeptide which is capable of interacting with a target peptide, e.g., a receptor, but which does not promote the activation of the receptor. The antagonist can also be a nucleic acid encoding a dominant negative form of a polypeptide, an antisense nucleic acid, or a ribozyme capable of interacting specifically with an RNA. Yet other antagonists are molecules which bind to a polypeptide and inhibit its action. Such molecules include peptides, e.g., forms of target peptides which do not have biological activity, and which inhibit binding to receptors. Thus, such peptides will bind to the active site of a protein and prevent it from interacting with target peptides. Yet other antagonists include antibodies that specifically interact with an epitope of a molecule, such that binding interferes with the biological function of the polypeptide. In yet another preferred embodiment, the antagonist is a small molecule, such as a molecule capable of inhibiting the interaction between a polypeptide and a target receptor. Alternatively, the small molecule can function as an antagonist by interacting with sites other than the receptor binding site.

Modulators of IL-1 (e.g. IL-1α, IL-1β or IL-1 receptor antagonist) or a protein encoded by a gene that is in linkage disequilibrium with an IL-1 gene can comprise any type of compound, including a protein, peptide, peptidomimetic, small molecule, or nucleic acid. Preferred agonists include nucleic acids (e.g. encoding an IL-1 protein or a gene that is up- or down-regulated by an IL-1 protein), proteins (e.g. IL-1 proteins or a protein that is up- or down-regulated thereby) or a small molecule (e.g. that regulates expression or binding of an IL-1 protein). Preferred antagonists, which can be identified, for example, using the assays described herein, include nucleic acids (e.g. single (antisense) or double stranded (triplex) DNA or PNA and ribozymes), protein (e.g. antibodies) and small molecules that act to suppress or inhibit IL-1 transcription and/or protein activity.

Effective Dose

Toxicity and therapeutic efficacy of such compounds can be determined by standard pharmaceutical procedures in cell cultures or experimental animals, e.g., for determining The $LD_{50}$ (the dose lethal to 50% of the population) and the $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Formulation and Use

Compositions for use in accordance with the present invention may be formulated in a conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and filsidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Assays to Identify Therapeutics

Based on the identification of mutations that cause or contribute to the development of osteoporosis, the invention further features cell-based or cell free assays for identifying therapeutics. In one embodiment, a cell expressing an IL-1 receptor, or a receptor for a protein that is encoded by a gene which is in linkage disequilibrium with an IL-1 gene, on the outer surface of its cellular membrane is incubated in the presence of a test compound alone or in the presence of a test compound and another protein and the interaction between the test compound and the receptor or between the protein (preferably a tagged protein) and the receptor is detected, e.g., by using a microphysiometer (McConnell et al. (1992) Science 257:1906). An interaction between the receptor and either the test compound or the protein is detected by the microphysiometer as a change in the acidification of the medium. This assay system thus provides a means of identifying molecular antagonists which, for example, function by interfering with protein- receptor interactions, as well as molecular agonist which, for example, function by activating a receptor.

Cellular or cell-free assays can also be used to identify compounds which modulate expression of an IL-1 gene or a gene in linkage disequilibrium therewith, modulate translation of an mRNA, or which modulate the stability of an mRNA or protein. Accordingly, in one embodiment, a cell which is capable of producing an IL-1, or other protein is incubated with a test compound and the amount of protein produced in the cell medium is measured and compared to that produced from a cell which has not been contacted with the test compound. The specificity of the compound vis a vis the protein can be confirmed by various control analysis, e.g., measuring the expression of one or more control gene. In particular, this assay can be used to determine the efficacy of antisense, ribozyme and triplex compounds.

Cell-free assays can also be used to identify compounds which are capable of interacting with a protein, to thereby modify the activity of the protein. Such a compound can, e.g., modify the structure of a protein thereby effecting its ability to bind to a receptor. In a preferred embodiment, cell-free assays for identifying such compounds consist essentially in a reaction mixture containing a protein and a test compound or a library of test compounds in the presence or absence of a binding partner. A test compound can be, e.g., a derivative of a binding partner, e.g., a biologically inactive target peptide, or a small molecule.

Accordingly, one exemplary screening assay of the present invention includes the steps of contacting a protein or functional fragment thereof with a test compound or library of test compounds and detecting the formation of complexes. For detection purposes, the molecule can be labeled with a specific marker and the test compound or library of test compounds labeled with a different marker. Interaction of a test compound with a protein or fragment thereof can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the protein or functional fragment thereof is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) an IL-1 or other protein, (ii) an appropriate receptor, and (iii) a test compound; and (b) detecting interaction of the protein and receptor. A statistically significant change (potentiation or inhibition) in the interaction of the protein and receptor in the presence of the test compound, relative to the interaction in the absence of the test compound, indicates a potential antagonist (inhibitor). The compounds of this assay can be contacted simultaneously. Alternatively, a protein can first be contacted with a test compound for an appropriate amount of time, following which the receptor is added to the reaction mixture. The efficacy of the compound can be assessed by generating dose response curves from data obtained using various concentrations of the test compound. Moreover, a control assay can also be performed to provide a baseline for comparison.

Complex formation between a protein and receptor may be detected by a variety of techniques. Modulation of the formation of complexes can be quantitated using, for example, detectably labeled proteins such as radiolabeled, fluorescently labeled, or enzymatically labeled proteins or receptors, by immunoassay, or by chromatographic detection.

Typically, it will be desirable to immobilize either the protein or the receptor to facilitate separation of complexes from uncomplexed forms of one or both of the proteins, as well as to accommodate automation of the assay. Binding of protein and receptor can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the receptor, e.g. an $^{35}$S-labeled receptor, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of protein or receptor found in the bead fraction quantitated from the gel using standard electrophoretic techniques such as described in the appended examples. Other techniques for immobilizing proteins on matrices are also available for use in the subject assay. For instance, either protein or receptor can be immobilized utilizing conjugation of biotin and streptavidin. Transgenic animals can also be made to identify agonists and antagonists or to confirm the safety and efficacy of a candidate therapeutic. Transgenic animals of the invention can include non-human animals containing a restenosis causative mutation under the control of an appropriate endogenous promoter or under the control of a heterologous promoter.

The transgenic animals can also be animals containing a transgene, such as reporter gene, under the control of an appropriate promoter or fragment thereof. These animals are useful, e.g., for identifying drugs that modulate production of an IL-1 protein, such as by modulating gene expression. Methods for obtaining transgenic non-human animals are well known in the art. In preferred embodiments, the expression of the causative mutation is restricted to specific subsets of cells, tissues or developmental stages utilizing, for example, cis-acting sequences that control expression in the desired pattern. In the present invention, such mosaic expression of a protein can be essential for many forms of lineage analysis and can additionally provide a means to assess the effects of, for example, expression level which might grossly alter development in small patches of tissue within an otherwise normal embryo. Toward this end, tissue-specific regulatory sequences and conditional regulatory sequences can be used to control expression of the mutation in certain spatial patterns. Moreover, temporal patterns of expression can be provided by, for example, conditional recombination systems or prokaryotic transcriptional regulatory sequences. Genetic techniques, which allow for the expression of a mutation can be regulated via site-specific genetic manipulation in vivo, are known to those skilled in the art.

The transgenic animals of the present invention all include within a plurality of their cells a causative mutation transgene of the present invention, which transgene alters the phenotype of the "host cell". In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of Saccharomyces cerevisiae (O'Gorman et al. (1991) Science 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) J. Biol. Chem. 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of the causative mutation transgene can be regulated via control of recombinase expression.

Use of the cre/loxP recombinase system to regulate expression of a causative mutation transgene requires the construction of a transgenic animal containing transgenes encoding both the Cre recombinase and the subject protein. Animals containing both the Cre recombinase and the restenosis causative mutation transgene can be provided through the construction of "double" transgenic animals. A convenient method for providing such animals is to mate two transgenic animals each containing a transgene.

Similar conditional transgenes can be provided using prokaryotic promoter sequences which require prokaryotic proteins to be simultaneous expressed in order to facilitate expression of the transgene. Exemplary promoters and the corresponding transactivating prokaryotic proteins are given in U.S. Pat. No. 4,833,080.

Moreover, expression of the conditional transgenes can be induced by gene therapy-like methods wherein a gene encoding the transactivating protein, e.g. a recombinase or a prokaryotic protein, is delivered to the tissue and caused to be expressed, such as in a cell-type specific manner. By this method, the transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) PNAS 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. Further, in such embodiments the sequence will be attached to a transcriptional control element, e.g., a promoter, which preferably allows the expression of the transgene product in a specific type of cell.

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo,* Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156;Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

The present invention is further illustrated by the following examples which should not be construed as limiting in any way. The contents of all cited references (including literature references, issued patents, published patent applications as cited throughout this application) are hereby expressly incorporated by reference. The practice of the present invention will employ, unless otherwise indicated, conventional techniques that are within the skill of the art. Such techniques are explained fully in the literature. See, for example, Molecular Cloning A Laboratory Manual, (2nd ed., Sambrook, Fritsch and Maniatis, eds., Cold Spring Harbor Laboratory Press: 1989); DNA Cloning, Volumes I and II (D. N. Glover ed., 1985); Oligonucleotide Synthesis (M. J. Gait ed., 1984); U.S. Pat. Nos. 4,683,195; 4,683,202; and Nucleic Acid Hybridization (B. D. Hames & S. J. Higgins eds., 1984).

EXAMPLES

Example 1
Osteoporosis Association Studies
UCSF Association Study

A cohort of 1,071 subjects participating in the Study of Osteoporotic Fractures of the University of California at San Francisco Association was genotyped for genotypic markers in the IL-1 gene cluster, using techniques, which are known in the art.

The results of the genotyping are presented in Table 1A. Table 1B presents the results of a Hawaiian osteoporosis study, which is further described below.

TABLE 1

Frequency counts of IL-1 gene cluster genotype markers

| Genotype | IL-1A (4845) | IL-1B (3954) | IL-1B (−511) | IL-1RN (2018) |
|---|---|---|---|---|
| A. UCSF Study of Osteoporotic Fractures (n = 1,071 Caucasian women) | | | | |
| 1.1 | 516 (48.2%) | 633 (59.1%) | 442 (41.3%) | 551 (51.4%) |
| 1.2 | 450 (42%) | 377 (35.2%) | 496 (46.3%) | 434 (40.5%) |
| 2.2 | 104 (9.7%) | 60 (5.6%) | 132 (12.3%) | 85 (7.9%) |
| missing | 1 | 1 | 1 | 1 |
| B. Hawaii Osteoporosis Study (n = 208 Japanese-American women) | | | | |
| 1.1 | 169 (82%) | 186 (89.4%) | 60 (29%) | 190 (91.3%) |
| 1.2 | 35 (17%) | 22 (10.6%) | 103 (49.8%) | 18 (8.7%) |
| 2.2 | 2 (1%) | – (0%) | 44 (21.3%) | – (0%) |
| missing | 2 | — | 1 | — |

In the random sample control cohort of 626 subjects, 185 non-spine fractures had occurred. These subjects were used for the analysis of "non-spine fractures".

TABLE 2

Genotype frequencies in cases, controls, and cohort sample in UCSF SOF study

| | | Hip Fracture | | Vertebral Fracture | | Wrist Fracture | | |
|---|---|---|---|---|---|---|---|---|
| | | Cases (n = 216) | Controls (n = 575) | Cases (n = 183) | Controls (n = 588) | Cases (n = 216) | Controls (n = 512) | Cohort* (n = 626) |
| IL-1A (+4845) | 1.1 | 106 (49%) | 283 (49%) | 88 (48%) | 287 (49%) | 100 (46%) | 254 (50%) | 308 (49%) |
| | 1.2 | 96 (44%) | 237 (41%) | 78 (43%) | 240 (41%) | 93 (43%) | 213 (42%) | 257 (41%) |
| | 2.2 | 14 (7%) | 55 (10%) | 17 (9%) | 61 (10%) | 23 (11%) | 45 (66%) | 61 (10%) |
| IL-1B (+3954) | 1.1 | 133 (61%) | 336 (58%) | 109 (59%) | 340 (58%) | 123 (57%) | 299 (58%) | 365 (58%) |
| | 1.2 | 75 (35%) | 199 (35%) | 67 (37%) | 207 (35%) | 82 (38%) | 180 (35%) | 219 (35%) |

TABLE 2-continued

Genotype frequencies in cases, controls, and cohort sample in UCSF SOF study

| | | Hip Fracture | | Vertebral Fracture | | Wrist Fracture | | |
| --- | --- | --- | --- | --- | --- | --- | --- | --- |
| | | Cases (n = 216) | Controls (n = 575) | Cases (n = 183) | Controls (n = 588) | Cases (n = 216) | Controls (n = 512) | Cohort* (n = 626) |
| | 2.2 | 8 (4%) | 40 (7%) | 7 (4%) | 41 (7%) | 11 (5%) | 33 (7%) | 42 (7%) |
| IL-1B (−511) | 1.1 | 98 (45%) | 230 (40%) | 82 (45%) | 228 (39%) | 92 (43%) | 203 (40%) | 247 (40%) |
| | 1.2 | 87 (40%) | 275 (48%) | 77 (42%) | 291 (49%) | 98 (45%) | 246 (48%) | 303 (48%) |
| | 2.2 | 31 (15%) | 70 (12%) | 24 (13%) | 67 (12%) | 26 (12%) | 63 (12%) | 76 (12%) |
| IL-1RN (+2018) | 1.1 | 116 (54%) | 294 (51%) | 95 (52%) | 304 (52%) | 110 (51%) | 264 (52%) | 322 (51%) |
| | 1.2 | 83 (38%) | 239 (42%) | 73 (40%) | 246 (42%) | 81 (37%) | 215 (42%) | 262 (42%) |
| | 2.2 | 17 (8%) | 42 (7%) | 15 (8%) | 38 (6%) | 25 (12%) | 33 (6%) | 42 (7%) |

*Includes 185 non-spine fracture subjects

As shown in Table 2, allele 2 of IL-1A (+4845) is associated with an increase in the risk of non-spine fractures. In addition, allele 2 of IL-1B (+3954) is associated with a statistically significant increase in the risk of non-spine fractures. In contrast, allele 2 of IL-1RN (+2018) is associated with a significant decrease in the risk of non-spine fractures. Allele 2 of IL-1A (+4845) is associated with an increase in wrist fractures, although not statistically significant (RR=1.8, 95% CI=1.0–3.5). In the total cohort, allele 2 is associated with an increase in risk of wrist fractures. This effect disappears when HRT users are excluded.

Increase in risk of fractures shows a gene-dose effect for allele 2 of IL-1A (+4845) and IL-1B (+3954). In particular, the more copies of allele 2, the larger the effect. Decrease of risk of fractures also shows a gene-dose effect for allele 2 of IL-1RN (+2018). Specifically, the more copies of allele 2, the larger the effect. As shown in Table 3A, these associations are true for the cohort with exclusion of HRT users. As shown in Table 3B, the associations hold up, though not as strong, when the total cohort, including HRT users, is considered. Hip fractures and vertebral spine fractures, on the other hand, do not appear to be associated with any of the IL-1 genetic markers.

TABLE 3A

IL-1 Genotype and Fractures, excluding HRT users

| | unadjusted | age/BMI adjusted | Multiple* adjusted |
| --- | --- | --- | --- |
| Non-spine Fracture, RH (95% CI) | | | |
| IL-1B (+4845) | | | |
| 1.1 | 1.0 (REF) | 1.0 (REF) | 1.0 (REF) |
| 1.2 | | 1.0 (0.7, 1.4) | 1.0 (0.7, 1.4) |
| 2.2 | | 1.4 (0.8, 2.5) | 1.6 (0.9, 2.8) |
| IL-1B (+3954) | | | |
| 1.1 | 1.0 (REF) | 1.0 (REF) | 1.0 (REF) |
| 1.2 | | 1.1 (0.8, 2.5) | 1.3 (0.9, 2.8) |
| 2.2 | | 1.8 (1.0, 3.3) | 2.0 (1.1, 3.8)# |
| IL-1RA (+2018) | | | |
| 1.1 | 1.0 (REF) | 1.0 (REF) | 1.0 (REF) |
| 1.2 | | 0.9 (0.6, 1.3) | 0.8 (0.6, 1.2) |
| | | 0.4 (0.2, 1.0) | 0.4 (0.2, 0.9)# |

TABLE 3A-continued

IL-1 Genotype and Fractures, excluding HRT users

| | unadjusted | age/BMI adjusted | Multiple* adjusted |
| --- | --- | --- | --- |
| Wrist Fracture, RH (95% CI) | | | |
| IL-1B (+4845) | | | |
| 1.1 | 1.0 REF | 1.0 (REF) | 1.0 (REF) |
| 1.2 | | 1.2 (0.8, 1.7) | 1.1 (0.7, 1.7) |
| | | 1.8 (0.9, 3.4) | 1.8 (1.0, 3.5) |

*adjusted for age, modified BMI, yrs since menopause, current smoking & alcohol, ERT use, thiaz diuretic use, self-reported health status and diabetes
p < 0.05 versus type 1.1

TABLE 3B

IL-1 Genotype and Fractures, including HRT user (total cohort)

| | unadjusted | age/BMI adjusted | multiple* adjusted |
| --- | --- | --- | --- |
| Non-spine Fracture, RH (95% CI) | | | |
| IL-1A (+4845) | | | |
| 1.1 | 1.0 (REF) | 1.0 (REF) | 1.0 (REF) |
| 1.2 | | 1.0 (0.7, 1.3) | 0.9 (0.7, 1.3) |
| 2.2 | | 1.2 (0.8, 2.0) | 1.3 (0.8, 2.1) |
| IL-1B (+3954) | | | |
| 1.1 | 1.0 (REF) | 1.0 (REF) | 1.0 (REF) |
| 1.2 | | 1.2 (0.9, 1.6) | 1.3 (0.9, 1.7) |
| 2.2 | | 1.4 (0.8, 2.3) | 1.4 (0.8, 2.4) |
| IL-1RA (+2018) | | | |
| 1.1 | 1.0 (REF) | 1.0 (REF) | 1.0 (REF) |
| 1.2 | | 0.9 (0.7, 1.2) | 0.9 (0.6, 1.2) |
| 2.2 | | 0.5 (0.2, 1.0)# | 0.5 (0.2, 1.0)# |

TABLE 3B-continued

IL-1 Genotype and Fractures, including HRT user (total cohort)

|  | unadjusted | age/BMI adjusted | multiple* adjusted |
|---|---|---|---|
| Wrist Fracture, RH (95% CI) | | | |
| IL-1B (+4845) | | | |
| 1.1 | 1.0 (REF) | 1.0 (REF) | 1.0 (REF) |
| 1.2 | 1.1 (0.8, 1.5) | 1.1 (0.8, 1.6) | 1.1 (0.8, 1.5) |
| 2.2 | 1.3 (0.8, 2.2) | 1.3 (0.8, 2.2) | 1.3 (0.7, 2.2) |
| TL-1RA (+2018) | | | |
| 1.1 | 1.0 (REF) | 1.0 (REF) | 1.0 (REF) |
| 1.2 | 0.9 (0.6, 1.2) | 0.9 (0.6, 1.2) | 0.9 (0.6, 1.2) |
| 2.2 | 1.8 (1.04, 3.0)# | 1.9 (1.1, 3.2)# | 1.9 (1.1, 3.3)# |

*adjusted for age, modified BMI, yrs since menopause, current smoking & alcohol, HRT use, thiaz diuretic use, self-reported health status and diabetes
p < 0.05 versus type 1.1

Bone mineral density (BMD) was measured at the calcaneus, distal radius, total hip, femoral neck and spine. The analysis was adjusted for age, bone mineral index (BMI) menopausal status and life style factors. As shown in Tables 4A and 4B, allele 2 of IL-1B (+3954) is associated with significantly higher BMD at the calcaneus, whether HRT users are included or excluded (p<0.05 for trend; p<0.05 for genotype [2.2] vs. genotype [1.1]).

Allele 2 of IL-1B (−511) is significantly associated with a lower BMD at the calcaneus in the total cohort, including HRT users (p<0.05 for trend; p<0.05 for genotype [2.2] vs. genotype [1.1]). Allele 2 of IL-1B (−511) is associated with a trend towards lower BMD at the calcaneus when HRT users are excluded. No consistent pattern of association between IL-1 genotypes and BMD at other sites was found.

TABLE 4A

IL-1 Genotype and Bone Mineral Density (n = 1,070)

|  | Mean calcaneal BMD (g/cm2) | | |
|---|---|---|---|
|  | unadjusted | age/BMI adjusted | Multiple* adjusted |
| IL-1B (+3954) | | | |
| 1.1 | .39 (.005) | .39 (.004) | .40 (.004) |
| 1.2 | .40 (.006) | .40 (.005) | .40 (.005) |
| 2.2 | .43 (.014)+,# | .42 (.012)+,# | .42 (.012)+,# |
| IL-1B (−511) | | | |
| 1.1 | .41 (.006) | .41 (.005) | .41 (.005) |
| 1.2 | .39 (.005)# | .40 (.005) | .39 (.005) # |
| 2.2 | .39 (.011)+,# | .39 (.009)+ | .39 (.009)+,# |

TABLE 4B

IL-1 Genotype and Bone Mineral Density, excluding HRT users

|  | Mean calcaneal BMD (g/cm2) | | |
|---|---|---|---|
|  | unadjusted | age/BMI adjusted | multiple* adjusted |
| IL-1B (+3954) | | | |
| 1.1 |  | .39 (.005) | .39 (.005) |
| 1.2 |  | .40 (.007) | .39 (.007) |
| 2.2 |  | .43 (.016)+ | .43 (.016) |

TABLE 4B-continued

IL-1 Genotype and Bone Mineral Density, excluding HRT users

|  | Mean calcaneal BMD (g/cm2) | | |
|---|---|---|---|
|  | unadjusted | age/BMI adjusted | multiple* adjusted |
| IL-1B (−511) | | | |
| 1.1 |  | .40 (.006) | .40 (.006) |
| 1.2 |  | .40 (.006) | .40 (.006) |
| 2.2 |  | .38 (.011) | .38 (.011) |

*adjusted for age, modified BMI, yrs since menopause, current smoking & alcohol, ERT use, thiazide diuretic use, self-reported health status and diabetes
+p(trend) < .05
p < .05 vs type 1.1

Rate of bone loss was measured at total hip, femoral neck and calcaneus. As shown in Tables 5A and 5B, allele 2 of IL-1B (−511) is associated with a higher rate of bone loss at the total hip (p<0.05 for trend), for the total cohort and for the cohort with exclusion of HRT users. Genotype [2.2] of IL-1B (−511) is associated with a trend towards a higher rate of bone loss at the calcaneus. Allele 2 of IL-1B (−511) is associated with a trend towards a higher rate of bone loss at the femoral neck. A gene-dose effect for rate of bone loss at the hip for allele 2 of IL-1B (−511) is present. A similar, though not significant association is observed for rate of bone loss at the femoral neck. These results are similar whether HRT users are included (Table 5A) or excluded (Table 5B) in the analysis.

Hawaiian Osteoporosis Study 100 participants in the Hawaii Osteoporosis Study with fractures and 100 participants without fractures were genotyped for genotypic markers in the IL-1 gene cluster. The results are presented in Table 1B. The participants in the study are all Japanese-American women in their early to mid 80's. The following clinical data were analyzed: spine and non-spine fractures, including and excluding ovariectomies, bone mineral content (BMC) at the distal and proximal radius, and os calcis, including and excluding subjects who had ovariectomies. The analysis was adjusted for age, BMI and duration of estrogen use.

Results

Allele 2 of IL-1A (+4845) is strongly associated with an increase in the number of spine and non-spine fractures (p<0.018), regardless whether subjects with or without ovariectomies were included.

Allele 2 of IL-1B (−511) is associated with a decrease in BMC of the distal radius (p<0.024). Allele 2 of IL-1RN (+2018) is associated with a decrease in BMC at the os calcis (p<0.022).

Discussion of Findings
Role of Ethnicity

The distribution of genotypes in the IL-1 gene cluster is very different for Americans with Caucasian ancestry and Japanese-Americans, many of whom in this specific study are first generation immigrants. Distinctly different distribution patterns have been found for other ethnic groups, notably:

Chinese (very low frequency of allele 2 of IL-1RN (+2018) and IL-1B (+3954));

African-Americans (pattern similar to the Japanese population); and

Hispanics (distribution pattern similar to European Caucasians. This is specifically true for Hispanics from European ancestry. However, the pattern is not very different in Mexican Hispanics with European ancestry).

Therefore the genotype of IL-1RN (+2018) may not accurately reflect the biological pattern and response. IL-1B (−511) may be a more accurate indicator for that specific haplotype and genotype pattern. Similarly, IL-1B (+3954) may not be an accurate marker for the haplotype pattern. IL-1A (+4954) may be a more accurate indicator for that specific haplotype and genotype pattern.

Fracture Risk

Allele 2 of IL-1A (+4845) and allele 2 of IL-1B (+3954) are associated with increase in fracture risk. This points to an association with haplotype pattern 1 (see FIG. 3) Calcaneal BMD is associated with allele 2 of IL-1B (+3954) (Haplotype pattern 1) Haplotype pattern 1 results in increased IL-1a and IL-1b levels and bioactivity, but normal IL-1 receptor antagonist levels.

Rate of Bone Loss

Rate of bone loss is associated with allele 2 of IL-1B (−511) (Haplotype pattern 2). Haplotype pattern 2 results in normal levels of IL-1, but reduced levels of IL-1 receptor antagonist. The net result is an increase in IL-1 biological activity and response.

Bone Mineral Density

BMD (or BMC) is associated with allele 2 of either IL-1B (−511) or IL-1RN (+2018) (Haplotype pattern 2) at the calcaneus, and at the distal radius.

Increase in BMD at the calcaneus is associated with haplotype pattern 2. BMD at other sites is not significantly associated with IL-1 markers in this study, which may be caused by the specifics of the study population resulting in a lack of power in the statistical analysis. Other issues that may play a role in the University of California, San Francisco study population are: better health, better education, participation in the study and a higher socioeconomic status.

The process of bone remodeling is regulated by a number of factors, including: bone metabolism, rate of bone loss, peak bone mass, life style factors, genetics, use of prescription drugs and body mass. Osteoporotic fractures are the endpoint in a complex process of bone remodeling, bone loss, and aging. Bone remodeling and thus the likelihood of developing osteoporosis and osteoprotic fractures are regulated by different biological processes at different stages of the life cycle. In the first 5–10 years after onset of menopause most rapid bone loss is experienced due to decrease of estrogen levels and increase of IL-1 levels and activity. In this stage increased formation and activation of osteoclasts (due to increased IL-1 levels) drives the process of bone remodeling. The increase in IL-1 levels in the first 5–10 years after menopause may be more important than levels of IL-1 receptor antagonist. Approximately 10 years after menopause, the rate of bone loss slows down, due to a change in the biology of bone remodeling. In this stage the reduced formation of osteoblasts forms the driving force behind bone remodeling. Reduced levels of IL-1 receptor antagonist may form a more important factor in later post-menopausal years in regulating the amount of bone loss.

Haplotype pattern 1 is associated with increase in IL-1a and IL-1b levels and bioactivity, but normal IL-1 receptor antagonist levels. Women with haplotype pattern 1 are likely to experience a larger bone loss during their early menopausal years than women with haplotype pattern 2. Women with haplotype pattern 1 are thus more likely to experience fractures at any stage of life, when no preventive measures or treatment are initiated. Women with haplotype pattern 2 will likely experience more bone loss later in life and may be more susceptible to experience fractures later in life, specifically fractures associated with age-related osteoporosis. Therefore, subjects with haplotype pattern 2, who produce constitutively less IL-1ra than subjects with haplotype pattern 1, will experience larger bone loss and reduced bone formation in the later postmenopausal phase of their life.

Based on the hypothesis set forth above, it follows that the data reported by Keen et al. (1998) ("Allelic variation in the interleukin-1 receptor antagonist gene is associated with early postmenopausal bone loss at the spine" (Bone 23 (4), 367–371): an association between allele [1] of the VNTR in IL-1RN and early postmenopausal bone loss) suggest that the subjects who have allele [1] of the VNTR actually carry haplotype pattern 1. Since all of the subjects in this study are within 5 years of onset of menopause, their bone loss is regulated by increased levels and activity of IL-1 and not by increased or decreased levels of IL-1ra. Since only the VNTR of IL-1RN was determined, the erroneous conclusion was reached that VNTR allele 1 of IL-1RN is important in the changes in bone density and is the main predictor for bone loss and risk of osteoporotic fracture incidence.

What is claimed is:

1. A method for determining whether a female subject has or is predisposed to developing osteoporosis comprising:
   detecting in the female subject an allele selected from the group consisting of: allele 2 of IL-1A (+4845), allele 2 of IL-1B (+3954) and allele 1 of IL-1B (−511), wherein the presence of the allele indicates that the female subject has or is predisposed to developing osteoporosis.

2. The method of claim 1, wherein the allele is detected by a method selected from the group consisting of:
   a) allele specific oligonucleotide hybridization;
   b) size analysis;
   c) sequencing;
   d) hybridization;
   e) 5' nuclease digestion;
   f) single-stranded conformation polymorphism;
   g) allele specific hybridization;
   h) primer specific extension; and
   j) oligonucleotide ligation assay.

3. The method of claim 1, wherein prior to or in conjunction with the detection step, a nucleic acid sample from the female subject is amplified.

4. The method of claim 2, wherein said size analysis is preceded by a restriction enzyme digestion step.

* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
tgtacctaag cccacccttt agagc                    25

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer -continued

```
<400> SEQUENCE: 2
tggcctccag aaacctccaa                                          20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
gctgatattc tggtgggaaa                                          20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
ggcaagagca aaactctgtc                                          20
```